(12) United States Patent
Nakai et al.

(10) Patent No.: US 11,572,637 B2
(45) Date of Patent: Feb. 7, 2023

(54) METHODS OF VIRAL NEUTRALIZING ANTIBODY EPITOPE MAPPING

(71) Applicant: OREGON HEALTH & SCIENCE UNIVERSITY, Portland, OR (US)

(72) Inventors: Hiroyuki Nakai, Portland, OR (US); Kei Adachi, Portland, OR (US)

(73) Assignee: Oregon Health & Science University, Portland, OR (US)

(*) Notice: Subject to any disclaimer, the term of this patent is extended or adjusted under 35 U.S.C. 154(b) by 260 days.

(21) Appl. No.: 16/922,935

(22) Filed: Jul. 7, 2020

(65) Prior Publication Data

US 2020/0333355 A1    Oct. 22, 2020

Related U.S. Application Data

(62) Division of application No. 15/306,429, filed as application No. PCT/US2015/027536 on Apr. 24, 2015, now Pat. No. 10,746,742.

(60) Provisional application No. 61/984,553, filed on Apr. 25, 2014.

(51) Int. Cl.
| | |
|---|---|
| *C40B 40/08* | (2006.01) |
| *C12N 15/86* | (2006.01) |
| *G01N 33/68* | (2006.01) |
| *C40B 30/04* | (2006.01) |

(52) U.S. Cl.
CPC ............ *C40B 40/08* (2013.01); *C12N 15/86* (2013.01); *G01N 33/6854* (2013.01); *C12N 2750/14121* (2013.01); *C12N 2750/14122* (2013.01); *C12N 2750/14143* (2013.01); *C40B 30/04* (2013.01)

(58) Field of Classification Search
None
See application file for complete search history.

(56) References Cited

U.S. PATENT DOCUMENTS

2016/0017295 A1* 1/2016 Schaffer .................. A61P 35/00
435/235.1

* cited by examiner

*Primary Examiner* — Christian C Boesen
(74) *Attorney, Agent, or Firm* — Stoel Rives LLP

(57) ABSTRACT

Disclosed herein are methods of high-throughput mapping of viral neutralizing antibody epitopes. Also disclosed are in vitro immunoprecipitation-based adeno-associated virus Barcode-Seq-based methods of mapping viral neutralizing antibody epitopes. In some embodiments, a method of high-throughput mapping of viral NtAb conformational epitopes can be utilized, which may comprise HP scanning of mutant viral libraries, immunoprecipitation (IP), and/or next-generation sequencing (NGS) technology. In some embodiments, a method of identifying one or more dominant epitopes in a viral vector may comprise contacting a mutant capsid of a virus with serum from a subject previously exposed to the virus and immunoprecipitating serum immunoglobulins from the serum. In various embodiments, the viral vector may be an AAV vector.

2 Claims, 20 Drawing Sheets

Specification includes a Sequence Listing.

(1) Produce each AAV mutant / serotype and control virus in separate dishes on a small scale (10-15 cm dishes).

(2) Make a pool of all viral clones produced on a small scale, and purify it as one DNA-barcoded AAV library.

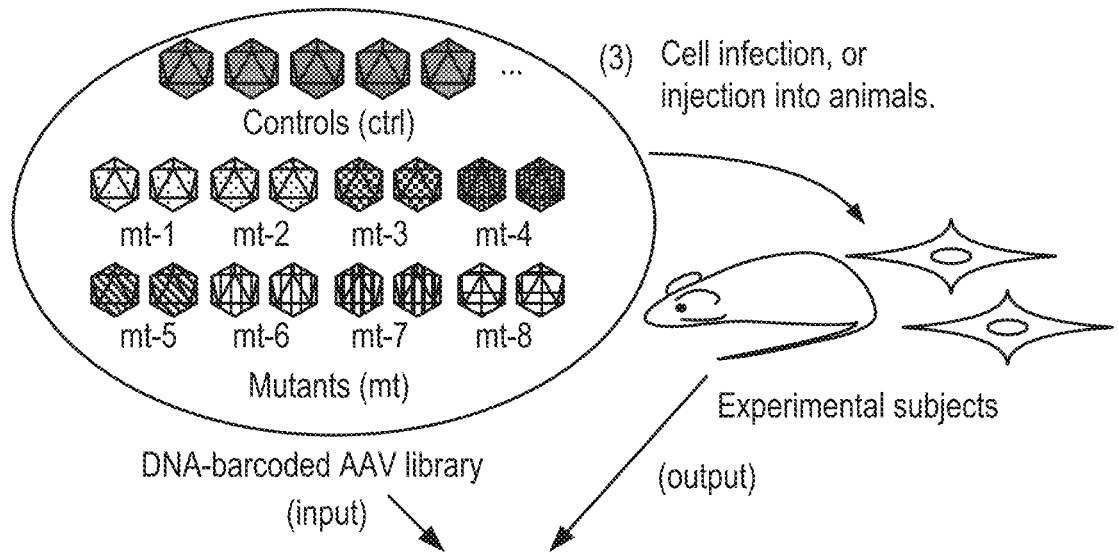

(3) Cell infection, or injection into animals.

(4) Recover viral genome DNA and PCR-amplify both input and output barcodes.

(5) Illumina-sequence barcodes, and determine output / input barcode sequence read no. ratios.

(6) Bioinformatic comparison.

PD > 1: increased
PD = 1: no change
PD < 1: decreased
compared to the control (ctrl)

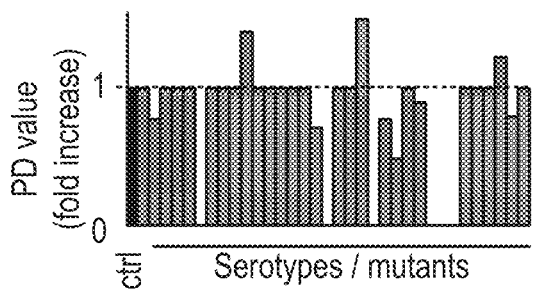

FIG. 1D

| AAV2R585E | YYLSRTNTPS-GTTTQSRL (443-460) | |
|---|---|---|
| 445-16000 | ..LNRTQN........... | (SEQ ID NO:24) |
| 445-00700 | ..LARTQS........... | (SEQ ID NO:25) |
| 445-00080 | ..LSRTQT........... | (SEQ ID NO:26) |
| 445-00009 | ..LSKTIN........... | (SEQ ID NO:27) |
| 447-16000 | ....RTQNQS......... | (SEQ ID NO:28) |
| 447-00700 | ....RTQSNPG........ | (SEQ ID NO:29) |
| 447-00080 | ....RTQTTG......... | (SEQ ID NO:30) |
| 447-00009 | ....KTING-......... | (SEQ ID NO:31) |
| 449-16000 | ......QNQS.GS...... | (SEQ ID NO:32) |
| 449-00700 | ......QSNPGG....... | (SEQ ID NO:33) |
| 449-00009 | ......INGS.G-...... | (SEQ ID NO:34) |
| 451-16000 | ........QS.GSAQ.... | (SEQ ID NO:35) |
| 451-00700 | ........NPGGTAG.... | (SEQ ID NO:36) |
| 451-00080 | ........TG.GTAN.... | (SEQ ID NO:37) |
| 451-00009 | ........GS.G-QN.... | (SEQ ID NO:38) |
| 453-16000 | ..........GSAQNK... | (SEQ ID NO:39) |
| 453-00700 | ..........GTAGNR... | (SEQ ID NO:40) |
| 453-00080 | ..........GTANTQ... | (SEQ ID NO:41) |
| 453-00009 | ..........S.G-QNQQ. | (SEQ ID NO:42) |
|  |  | (SEQ ID NO:43) |

| AAV9 | YYLSKTING-SGQNQQTL (445-461) | |
|---|---|---|
| 447-00002 | ..LSRTNT.......... | (SEQ ID NO:44) |
| 449-00002 | ....RTNTPS........ | (SEQ ID NO:45) |
| 451-00002 | ......NTPSGT...... | (SEQ ID NO:46) |
| 453-00002 | ........PSGTTT.... | (SEQ ID NO:47) |
| 454-00002 | ..........GTTTQS.. | (SEQ ID NO:48) |
|  |  | (SEQ ID NO:49) |

FIG. 4

SEQUENCE LISTING

```
<160> NUMBER OF SEQ ID NOS: 58

<210> SEQ ID NO 1
<211> LENGTH: 6
<212> TYPE: PRT
<213> ORGANISM: adeno-associated virus

<400> SEQUENCE: 1

Gln Ser Gly Ser Ala Gln
1               5

<210> SEQ ID NO 2
<211> LENGTH: 5
<212> TYPE: PRT
<213> ORGANISM: adeno-associated virus

<400> SEQUENCE: 2

Gly Ser Gly Gln Asn
1               5

<210> SEQ ID NO 3
<211> LENGTH: 6
<212> TYPE: PRT
<213> ORGANISM: adeno-associated virus

<400> SEQUENCE: 3

Pro Ser Gly Thr Thr Thr
1               5
```

```
<210> SEQ ID NO 4
<211> LENGTH: 11
<212> TYPE: PRT
<213> ORGANISM: adeno-associated virus

<400> SEQUENCE: 4

Arg Thr Gln Ser Asn Pro Gly Gly Thr Ala Gly
1               5                   10

<210> SEQ ID NO 5
<211> LENGTH: 8
<212> TYPE: PRT
<213> ORGANISM: adeno-associated virus

<400> SEQUENCE: 5

Gln Ser Gly Ser Ala Gln Asn Lys
1               5

<210> SEQ ID NO 6
<211> LENGTH: 7
<212> TYPE: PRT
<213> ORGANISM: adeno-associated virus

<400> SEQUENCE: 6

Asn Pro Gly Gly Thr Ala Gly
1               5

<210> SEQ ID NO 7
<211> LENGTH: 736
<212> TYPE: PRT
<213> ORGANISM: adeno-associated virus

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205
```

```
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Ser Ser Asn Asp Asn
                260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
```

```
                625                 630                 635                 640
Lys His Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 8
<211> LENGTH: 736
<212> TYPE: PRT
<213> ORGANISM: adeno-associated virus

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270
```

-continued

Ala Tyr Phe Gly Tyr Ser Thr Pro Trp Gly Tyr Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Thr Val Gln Val Phe Thr Asp Ser Asp Tyr Gln Leu
            340                 345                 350

Pro Tyr Val Ala Ala Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn

```
                690                 695                 700
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 9
<211> LENGTH: 736
<212> TYPE: PRT
<213> ORGANISM: adeno-associated virus

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Leu Thr Met Ala Ser Gly Gly Gly
    195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335
```

-continued

```
Asn Leu Thr Ser Thr Val Gln Val Phe Thr Asp Ser Asp Tyr Gln Leu
            340                 345                 350
Pro Tyr Val Leu Gly Ala Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 10
<211> LENGTH: 736
<212> TYPE: PRT

<213> ORGANISM: adeno-associated virus

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala Ala Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

```
Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460
```

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Ala Ala Leu
            725                 730                 735

<210> SEQ ID NO 12
<211> LENGTH: 736
<212> TYPE: PRT
<213> ORGANISM: adeno-associated virus

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

-continued

```
Asn Leu Gly Arg Ala Val Phe Gln Ala Lys Lys Arg Leu Leu Glu Pro
            115                 120                 125
Leu Gly Leu Val Glu Glu Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
```

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Ala
                725                 730                 735

<210> SEQ ID NO 13
<211> LENGTH: 15
<212> TYPE: PRT
<213> ORGANISM: adeno-associated virus

<400> SEQUENCE: 13

Tyr Leu Tyr Tyr Leu Ser Arg Thr Asn Thr Pro Ser Gly Thr Thr
1               5                   10                  15

<210> SEQ ID NO 14
<211> LENGTH: 15
<212> TYPE: PRT
<213> ORGANISM: adeno-associated virus

<400> SEQUENCE: 14

Tyr Leu Tyr Tyr Leu Asn Arg Thr Asn Thr Pro Ser Gly Thr Thr
1               5                   10                  15

<210> SEQ ID NO 15
<211> LENGTH: 15
<212> TYPE: PRT
<213> ORGANISM: adeno-associated virus

<400> SEQUENCE: 15

Tyr Leu Tyr Tyr Leu Asn Arg Thr Asn Thr Pro Ser Gly Thr Thr
1               5                   10                  15

<210> SEQ ID NO 16
<211> LENGTH: 15
<212> TYPE: PRT
<213> ORGANISM: adeno-associated virus

<400> SEQUENCE: 16

Tyr Leu Tyr Tyr Leu Ala Arg Thr Asn Thr Pro Ser Gly Thr Thr
1               5                   10                  15

<210> SEQ ID NO 17
<211> LENGTH: 15
<212> TYPE: PRT
<213> ORGANISM: adeno-associated virus

<400> SEQUENCE: 17

Tyr Leu Tyr Tyr Leu Ser Arg Thr Asn Thr Pro Ser Gly Thr Thr
1               5                   10                  15

<210> SEQ ID NO 18
<211> LENGTH: 15
<212> TYPE: PRT
<213> ORGANISM: adeno-associated virus

<400> SEQUENCE: 18

Tyr Leu Tyr Tyr Leu Ser Arg Thr Asn Thr Pro Ser Gly Thr Thr
1               5                   10                  15

<210> SEQ ID NO 19
<211> LENGTH: 15
<212> TYPE: PRT
<213> ORGANISM: adeno-associated virus

<400> SEQUENCE: 19

Tyr Leu Tyr Tyr Leu Asn Arg Thr Asn Thr Pro Ser Gly Thr Thr
1               5                   10                  15

<210> SEQ ID NO 20
<211> LENGTH: 15
<212> TYPE: PRT
<213> ORGANISM: adeno-associated virus

<400> SEQUENCE: 20

Tyr Leu Tyr Tyr Leu Asn Arg Thr Asn Thr Pro Ser Gly Thr Thr
1               5                   10                  15

<210> SEQ ID NO 21
<211> LENGTH: 15
<212> TYPE: PRT
<213> ORGANISM: adeno-associated virus

<400> SEQUENCE: 21

Tyr Leu Tyr Tyr Leu Ala Arg Thr Asn Thr Pro Ser Gly Thr Thr
1               5                   10                  15

<210> SEQ ID NO 22
<211> LENGTH: 15
<212> TYPE: PRT
<213> ORGANISM: adeno-associated virus

<400> SEQUENCE: 22

Tyr Leu Tyr Tyr Leu Ser Arg Thr Asn Thr Pro Ser Gly Thr Thr
1               5                   10                  15

<210> SEQ ID NO 23
<211> LENGTH: 15
<212> TYPE: PRT
<213> ORGANISM: adeno-associated virus

<400> SEQUENCE: 23

Tyr Leu Tyr Tyr Leu Ser Lys Thr Asn Thr Pro Ser Gly Thr Thr

<210> SEQ ID NO 24
<211> LENGTH: 18
<212> TYPE: PRT
<213> ORGANISM: adeno-associated virus

<400> SEQUENCE: 24

Tyr Tyr Leu Ser Arg Thr Asn Thr Pro Ser Gly Thr Thr Thr Gln Ser
1               5                   10                  15

Arg Leu

<210> SEQ ID NO 25
<211> LENGTH: 18
<212> TYPE: PRT
<213> ORGANISM: adeno-associated virus

<400> SEQUENCE: 25

Tyr Tyr Leu Asn Arg Thr Gln Asn Pro Ser Gly Thr Thr Thr Gln Ser
1               5                   10                  15

Arg Leu

<210> SEQ ID NO 26
<211> LENGTH: 18
<212> TYPE: PRT
<213> ORGANISM: adeno-associated virus

<400> SEQUENCE: 26

Tyr Tyr Leu Ala Arg Thr Gln Ser Pro Ser Gly Thr Thr Thr Gln Ser
1               5                   10                  15

Arg Leu

<210> SEQ ID NO 27
<211> LENGTH: 18
<212> TYPE: PRT
<213> ORGANISM: adeno-associated virus

<400> SEQUENCE: 27

Tyr Tyr Leu Ser Arg Thr Gln Thr Pro Ser Gly Thr Thr Thr Gln Ser
1               5                   10                  15

Arg Leu

<210> SEQ ID NO 28
<211> LENGTH: 18
<212> TYPE: PRT
<213> ORGANISM: adeno-associated virus

<400> SEQUENCE: 28

Tyr Tyr Leu Ser Lys Thr Ile Asn Pro Ser Gly Thr Thr Thr Gln Ser
1               5                   10                  15

Arg Leu

<210> SEQ ID NO 29
<211> LENGTH: 18
<212> TYPE: PRT
<213> ORGANISM: adeno-associated virus

<400> SEQUENCE: 29

Tyr Tyr Leu Ser Arg Thr Gln Asn Gln Ser Gly Thr Thr Thr Gln Ser
1               5                   10                  15

Arg Leu

<210> SEQ ID NO 30
<211> LENGTH: 19
<212> TYPE: PRT
<213> ORGANISM: adeno-associated virus

<400> SEQUENCE: 30

Tyr Tyr Leu Ser Arg Thr Gln Ser Asn Pro Gly Gly Thr Thr Thr Gln
1               5                   10                  15

Ser Arg Leu

<210> SEQ ID NO 31
<211> LENGTH: 18
<212> TYPE: PRT
<213> ORGANISM: adeno-associated virus

<400> SEQUENCE: 31

Tyr Tyr Leu Ser Arg Thr Gln Thr Thr Gly Gly Thr Thr Thr Gln Ser
1               5                   10                  15

Arg Leu

<210> SEQ ID NO 32
<211> LENGTH: 17
<212> TYPE: PRT
<213> ORGANISM: adeno-associated virus

<400> SEQUENCE: 32

Tyr Tyr Leu Ser Lys Thr Ile Asn Gly Gly Thr Thr Thr Gln Ser Arg
1               5                   10                  15

Leu

<210> SEQ ID NO 33
<211> LENGTH: 18
<212> TYPE: PRT
<213> ORGANISM: adeno-associated virus

<400> SEQUENCE: 33

Tyr Tyr Leu Ser Arg Thr Gln Asn Gln Ser Gly Ser Thr Thr Gln Ser
1               5                   10                  15

Arg Leu

<210> SEQ ID NO 34
<211> LENGTH: 19
<212> TYPE: PRT
<213> ORGANISM: adeno-associated virus

<400> SEQUENCE: 34

Tyr Tyr Leu Ser Arg Thr Gln Ser Asn Pro Gly Gly Thr Thr Thr Gln
1               5                   10                  15

Ser Arg Leu

<210> SEQ ID NO 35
<211> LENGTH: 17
<212> TYPE: PRT
<213> ORGANISM: adeno-associated virus

<400> SEQUENCE: 35

Tyr Tyr Leu Ser Arg Thr Ile Asn Gly Ser Gly Thr Thr Gln Ser Arg
1               5                   10                  15

Leu

```
<210> SEQ ID NO 36
<211> LENGTH: 18
<212> TYPE: PRT
<213> ORGANISM: adeno-associated virus

<400> SEQUENCE: 36

Tyr Tyr Leu Ser Arg Thr Asn Thr Gln Ser Gly Ser Ala Gln Gln Ser
1               5                   10                  15

Arg Leu

<210> SEQ ID NO 37
<211> LENGTH: 19
<212> TYPE: PRT
<213> ORGANISM: adeno-associated virus

<400> SEQUENCE: 37

Tyr Tyr Leu Ser Arg Thr Asn Thr Asn Pro Gly Gly Thr Ala Gly Gln
1               5                   10                  15

Ser Arg Leu

<210> SEQ ID NO 38
<211> LENGTH: 18
<212> TYPE: PRT
<213> ORGANISM: adeno-associated virus

<400> SEQUENCE: 38

Tyr Tyr Leu Ser Arg Thr Asn Thr Thr Gly Gly Thr Ala Asn Gln Ser
1               5                   10                  15

Arg Leu

<210> SEQ ID NO 39
<211> LENGTH: 17
<212> TYPE: PRT
<213> ORGANISM: adeno-associated virus

<400> SEQUENCE: 39

Tyr Tyr Leu Ser Arg Thr Asn Thr Gly Ser Gly Gln Asn Gln Ser Arg
1               5                   10                  15

Leu

<210> SEQ ID NO 40
<211> LENGTH: 18
<212> TYPE: PRT
<213> ORGANISM: adeno-associated virus

<400> SEQUENCE: 40

Tyr Tyr Leu Ser Arg Thr Asn Thr Pro Ser Gly Ser Ala Gln Asn Lys
1               5                   10                  15

Arg Leu

<210> SEQ ID NO 41
<211> LENGTH: 18
<212> TYPE: PRT
<213> ORGANISM: adeno-associated virus

<400> SEQUENCE: 41

Tyr Tyr Leu Ser Arg Thr Asn Thr Pro Ser Gly Thr Ala Gly Asn Arg
1               5                   10                  15

Arg Leu
```

```
<210> SEQ ID NO 42
<211> LENGTH: 18
<212> TYPE: PRT
<213> ORGANISM: adeno-associated virus

<400> SEQUENCE: 42

Tyr Tyr Leu Ser Arg Thr Asn Thr Pro Ser Gly Thr Ala Asn Thr Gln
1               5                   10                  15

Arg Leu

<210> SEQ ID NO 43
<211> LENGTH: 17
<212> TYPE: PRT
<213> ORGANISM: adeno-associated virus

<400> SEQUENCE: 43

Tyr Tyr Leu Ser Arg Thr Asn Thr Pro Ser Gly Gln Asn Gln Gln Arg
1               5                   10                  15

Leu

<210> SEQ ID NO 44
<211> LENGTH: 17
<212> TYPE: PRT
<213> ORGANISM: adeno-associated virus

<400> SEQUENCE: 44

Tyr Tyr Leu Ser Lys Thr Ile Asn Gly Ser Gly Gln Asn Gln Gln Thr
1               5                   10                  15

Leu

<210> SEQ ID NO 45
<211> LENGTH: 17
<212> TYPE: PRT
<213> ORGANISM: adeno-associated virus

<400> SEQUENCE: 45

Tyr Tyr Leu Ser Arg Thr Asn Thr Gly Ser Gly Gln Asn Gln Gln Thr
1               5                   10                  15

Leu

<210> SEQ ID NO 46
<211> LENGTH: 18
<212> TYPE: PRT
<213> ORGANISM: adeno-associated virus

<400> SEQUENCE: 46

Tyr Tyr Leu Ser Arg Thr Asn Thr Pro Ser Gly Gln Asn Gln Gln
1               5                   10                  15

Thr Leu

<210> SEQ ID NO 47
<211> LENGTH: 18
<212> TYPE: PRT
<213> ORGANISM: adeno-associated virus

<400> SEQUENCE: 47

Tyr Tyr Leu Ser Lys Thr Asn Thr Pro Ser Gly Thr Gln Asn Gln Gln
1               5                   10                  15

Thr Leu

<210> SEQ ID NO 48
```

<211> LENGTH: 18
<212> TYPE: PRT
<213> ORGANISM: adeno-associated virus

<400> SEQUENCE: 48

Tyr Tyr Leu Ser Lys Thr Ile Asn Pro Ser Gly Thr Thr Thr Gln Gln
1               5                   10                  15
Thr Leu

<210> SEQ ID NO 49
<211> LENGTH: 17
<212> TYPE: PRT
<213> ORGANISM: adeno-associated virus

<400> SEQUENCE: 49

Tyr Tyr Leu Ser Lys Thr Ile Asn Gly Gly Thr Thr Thr Gln Ser Thr
1               5                   10                  15
Leu

<210> SEQ ID NO 50
<211> LENGTH: 6
<212> TYPE: PRT
<213> ORGANISM: adeno-associated virus

<400> SEQUENCE: 50

Ser Ser Gln Ser Gly Ala
1               5

<210> SEQ ID NO 51
<211> LENGTH: 8
<212> TYPE: PRT
<213> ORGANISM: adeno-associated virus

<400> SEQUENCE: 51

Ser Asn Ser Thr Ser Gly Gly Ser
1               5

<210> SEQ ID NO 52
<211> LENGTH: 8
<212> TYPE: PRT
<213> ORGANISM: adeno-associated virus

<400> SEQUENCE: 52

Arg Asp Ser Leu Val Asn Pro Gly
1               5

<210> SEQ ID NO 53
<211> LENGTH: 6
<212> TYPE: PRT
<213> ORGANISM: adeno-associated virus

<400> SEQUENCE: 53

Arg Asp Ser Leu Val Asn
1               5

<210> SEQ ID NO 54
<211> LENGTH: 6
<212> TYPE: PRT
<213> ORGANISM: adeno-associated virus

<400> SEQUENCE: 54

Ser Leu Val Asn Pro Gly
1               5

```
<210> SEQ ID NO 55
<211> LENGTH: 6
<212> TYPE: PRT
<213> ORGANISM: adeno-associated virus

<400> SEQUENCE: 55

Gln Asn Asp Gly Thr Thr
1               5

<210> SEQ ID NO 56
<211> LENGTH: 6
<212> TYPE: PRT
<213> ORGANISM: adeno-associated virus

<400> SEQUENCE: 56

Gln Gln Arg Val Ser Lys
1               5

<210> SEQ ID NO 57
<211> LENGTH: 6
<212> TYPE: PRT
<213> ORGANISM: adeno-associated virus

<400> SEQUENCE: 57

Asn Arg Gln Ala Ala Thr
1               5

<210> SEQ ID NO 58
<211> LENGTH: 5
<212> TYPE: PRT
<213> ORGANISM: adeno-associated virus

<400> SEQUENCE: 58

Gly Cys Gly Gln Asn
1               5
```

METHODS OF VIRAL NEUTRALIZING ANTIBODY EPITOPE MAPPING

RELATED APPLICATIONS

The present application is a divisional of U.S. patent application Ser. No. 15/306,429 titled METHODS OF VIRAL NEUTRALIZING ANTIBODY EPITOPE MAPPING, filed on Oct. 24, 2016, which is a U.S. National Phase patent application under 35. U.S.C. § 371 of International Application No. PCT/US2015/027536, filed Apr. 24, 2015, which claims priority to U.S. Provisional Patent Application No. 61/984,553, filed Apr. 25, 2014, all of which are each expressly incorporated herein by reference.

ACKNOWLEDGEMENT OF GOVERNMENT SUPPORT

This application was made with US Government support under grant number RO1DK078388 and NS088399, awarded by the National Institutes of Health. The US Government has certain rights in this application.

TECHNICAL FIELD

The disclosure generally relates to methods of high-throughput mapping of viral neutralizing antibody epitopes. More specifically, the disclosure relates to in vitro immunoprecipitation-based adeno-associated virus Barcode-Seq-based methods of mapping viral neutralizing antibody epitopes.

BACKGROUND

Viral neutralizing antibody (NtAb) epitope mapping can assist in the development of new vaccines and pharmaceuticals for the prevention and/or treatment of infectious diseases. Additionally, viral NtAb epitope mapping can assist in the development of gene delivery vectors. Identification of and knowledge regarding viral NtAb epitopes may help in the genetic engineering of components of viral vectors that may evade a host immune response, as the host immune response can be a significant obstacle to effective in vivo gene therapy.

Adeno-associated virus (AAV) is a promising in vivo gene delivery vector for gene therapy. Various issues remain to be overcome, however, in the use of AAV as an in vivo gene delivery vector, including the requirement of high vector dose for clinically beneficial outcomes, efficacy-limiting host immune response against viral proteins, promiscuous viral tropism, and the high prevalence of pre-existing anti-AAV neutralizing antibodies in humans. Despite these issues, interest in the use of AAV in gene therapy is growing. A number of naturally occurring serotypes and subtypes have been isolated from human and non-human primate tissues (Gao G et al., J Virol 78, 6381-6388 (2004) and Gao G et al., Proc Natl Acad Sci USA 99, 11854-11859 (2002), both of which are incorporated by reference herein). Among the newly-identified adeno-associated virus isolates, AAV serotype 8 (AAV8) and AAV serotype 9 (AAV9) have gained much attention because recombinant adeno-associated vectors (rAAVs) derived from these two serotypes can transduce various organs including the liver, heart, skeletal muscles, and central nervous system with high efficiency following systemic administration via the periphery (Foust K D et al., Nat Biotechnol 27, 59-65 (2009); Gao et al., 2004, supra; Ghosh A et al., Mol Ther 15, 750-755 (2007); Inagaki K et al., Mol Ther 14, 45-53 (2006); Nakai H et al., J Virol 79, 214-224 (2005); Pacak C A et al., Circ Res 99, e3-e9 (2006); Wang Z et al., Nat Biotechnol 23, 321-328 (2005); and Zhu T et al., Circulation 112, 2650-2659 (2005), all of which are incorporated by reference herein).

The robust transduction by rAAV8 and rAAV9 vectors has been presumed to be ascribed to strong tropism for these cell types, efficient cellular uptake of vectors, and/or rapid uncoating of virion shells in cells (Thomas C E et al., J Virol 78, 3110-3122 (2004), incorporated by reference herein). In addition, emergence of capsid-engineered rAAV with better performance has significantly broadened the utility of rAAV as a vector toolkit (Asokan A et al., Mol Ther 20, 699-708 (2012), incorporated by reference herein). Proof-of-concept for rAAV-mediated gene therapy has been shown in many preclinical animal models of human diseases. Phase I/II clinical studies have been initiated or completed for genetic diseases including hemophilia B (Manno C S et al., Nat Med 12, 342-347 (2006) and Nathwani A C et al., N Engl J Med 365, 2357-2365 (2011), both of which are incorporated by reference herein); muscular dystrophy (Mendell J R et al., N Engl J Med 363, 1429-1437 (2011), incorporated by reference herein); cardiac failure (Jessup M et al., Circulation 124, 304-313 (2011), incorporated by reference herein); blinding retinopathy (Maguire A M et al., Lancet 374, 1597-1605 (2009), incorporated by reference herein); and α1 anti-trypsin deficiency (Flotte T R et al., Hum Gene Ther 22, 1239-1247 (2011), incorporated by reference herein), among others.

Although rAAV vectors have widely been used in preclinical animal studies and have been tested in clinical safety studies, the current rAAV-mediated gene delivery systems remain suboptimal for broader clinical applications. The sequence of an AAV viral capsid protein defines numerous features of a particular AAV vector. For example, the capsid protein affects features such as capsid structure and assembly, interactions with AAV nonstructural proteins such as Rep and AAP proteins, interactions with host body fluids and extracellular matrix, clearance of the virus from the blood, vascular permeability, antigenicity, reactivity to NtAbs, tissue/organ/cell type tropism, efficiency of cell attachment and internalization, intracellular trafficking routes, and virion uncoating rates. Furthermore, the relationship between a given AAV capsid amino acid sequence and the characteristics of the rAAV vector are unpredictable.

High prevalence of pre-existing NtAbs against AAV capsids in humans poses a significant barrier to successful AAV vector-mediated gene therapy. There has been strong enthusiasm about developing "stealth" AAV vectors that can evade NtAbs; however, creation of such AAVs requires more comprehensive information about NtAb epitopes, which currently remains very limited.

DNA-barcoded AAV2R585E hexapeptide (HP) scanning capsid mutant libraries have been produced in which AAV2-derived HPs were replaced with those derived from other serotypes. These libraries have been injected intravenously into mice harboring anti-AAV1 or AAV9 capsid antibodies, which has led to the identification of 452-QSGSAQ-457 (SEQ ID NO:1) in the AAV1 capsid and 453-GSGQN-457 (SEQ ID NO:2) in the AAV9 capsid as epitopes for anti-AAV NtAbs in mouse sera (Adachi K et al., Nat Commun 5, 3075 (2014)). These epitopes correspond to the highest peak of the three-fold symmetry axis protrusion on the capsid. In addition, this region may also function as an epitope for mouse anti-AAV7 NtAbs using the same in vivo approach. A sequencing-based high-throughput approach, termed AAV Barcode-Seq, can allow characterization of phenotypes of hundreds of different AAV strains and can be applied to anti-AAV NtAb epitope mapping.

BRIEF DESCRIPTION OF THE FIGURES

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1D is a representation of a procedure for AAV Barcode-Seq analysis. PCR products obtained from each sample are indexed with sample-specific barcodes attached to the PCR primers. This allows multiplexed ILLUMINA sequencing. Phenotypic Difference (PD) values provide information about a spectrum of phenotypes (receptor binding, transduction, tropism, blood clearance, reactivity to NtAbs, blood-cerebrospinal fluid barrier (BCSFB) penetrability, etc.) for each serotype or mutant.

FIG. 4 depicts AAV2R585E and AAV9 HP scanning mutants included in the DNA/RNA-barcoded dsAAV-U6-VBCLib-1. The amino acid sequences around the highest peak of the AAV capsids derived from AAV2R585E, devoid of HP mutations and AAV2R585E-HP mutants, are aligned to the left and those derived from wild-type AAV9 and AAV9-HP mutants are aligned to the right. Bold letters and hyphens indicate amino acid mutations and deletions compared to the parental sequences, respectively. The name of each mutant is given to the amino acid sequences based on the naming system as follows. The left three digits indicate the first amino acid position of the hexapeptide based on AAV2 VP1 (left panel) and AAV9 VP1 (right panel). The right five digits indicate AAV serotype from which each hexapeptide is derived: 10000, AAV1; 06000, AAV6; 00700, AAV7; 00080, AAV8; 00009, AAV9; and 00002, AAV2. When a hexapeptide amino acid sequence is shared with multiple serotypes, the right five digits have more than one positive integer.

DETAILED DESCRIPTION

Figure 1A:
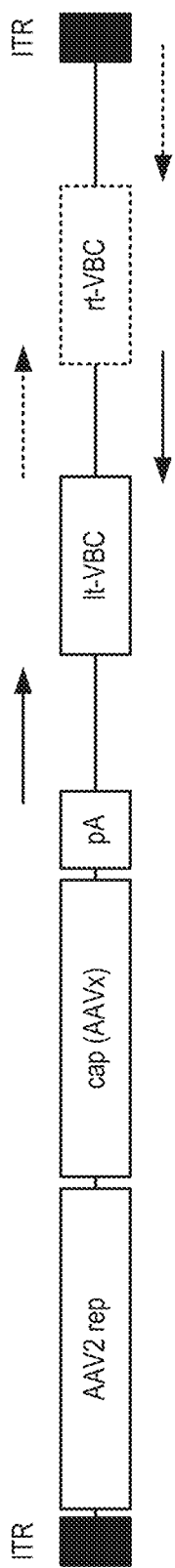
FIG. 1A depicts a map of the DNA-barcoded AAV genome containing a pair of 12 nucleotide-long DNA barcodes (lt-VBC and rt-VBC) downstream of the AAV2 pA. Each virus barcode (VBC) can be PCR-amplified separately.
Figure 1B:
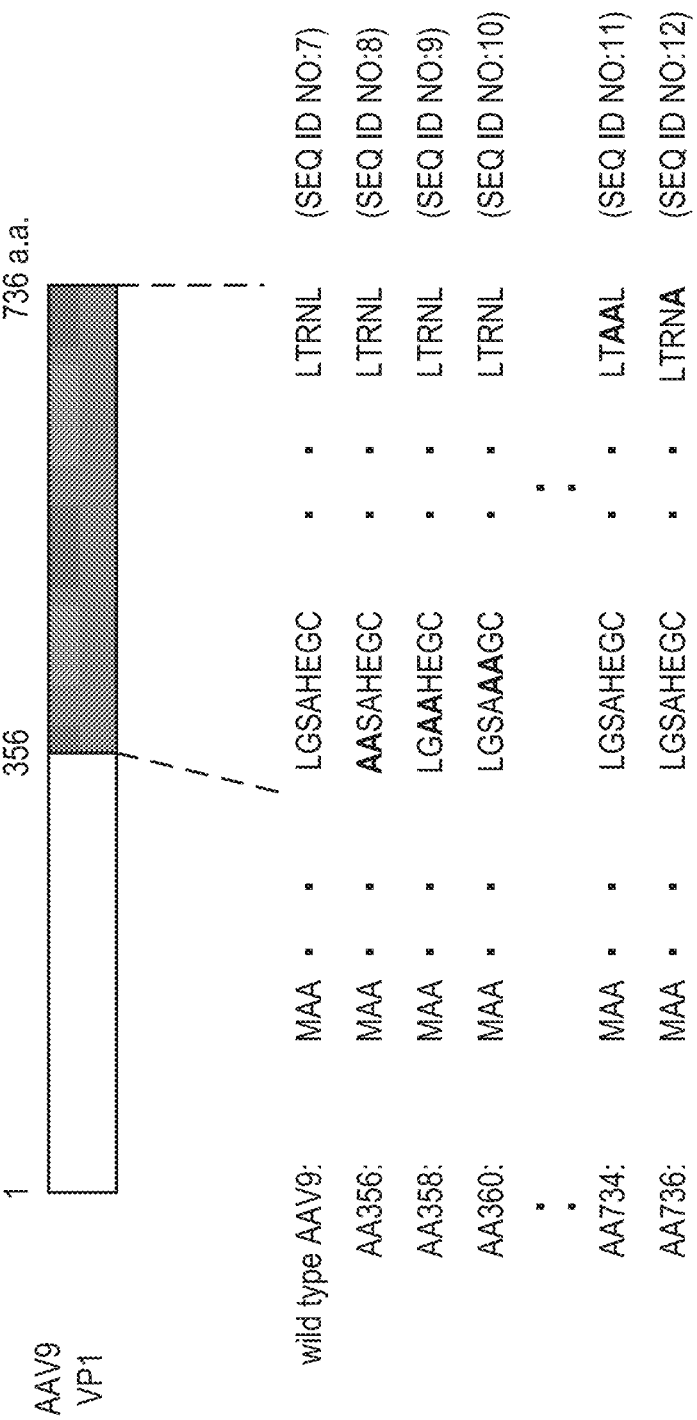
FIG. 1B is a representation of double alanine (AA) scanning mutagenesis of the AAV9 capsid.

It will be readily understood that the embodiments, as generally described herein, are exemplary. The following more detailed description of various embodiments is not intended to limit the scope of the present disclosure, but is merely representative of various embodiments. Moreover, the order of steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

The term "viral vector" as used herein means any vector that comprises or derives from components of a given virus and is suitable to infect mammalian cells, including human cells, of any of a number of tissue types, such as brain, heart, lung, skeletal muscle, liver, kidney, spleen, or pancreas, whether in vitro or in vivo. The term "viral vector" may be used to refer to a viral particle (or virion) comprising at least a nucleic acid molecule encoding a protein of interest.

The term "AAV vector" as used herein means any vector that comprises or derives from components of AAV and is suitable to infect mammalian cells, including human cells, of any of a number of tissue types, such as brain, heart, lung, skeletal muscle, liver, kidney, spleen, or pancreas, whether in vitro or in vivo. The term "AAV vector" may be used to refer to an AAV type viral particle (or virion) comprising at least a nucleic acid molecule encoding a protein of interest.

Additionally, the AAVs disclosed herein may be derived from various serotypes, including combinations of serotypes (e.g., "pseudotyped" AAV) or from various genomes (e.g., single-stranded or self-complementary). In particular embodiments, the AAV vectors disclosed herein may comprise desired proteins or protein variants. A "variant" as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both.

Methods of producing AAV vectors as disclosed herein are well known in the art, including methods, for example, using packaging cells, auxiliary viruses or plasmids, and/or baculovirus systems (see, e.g., Samulski et al., J Virol 63, 3822 (1989); Xiao et al., J Virol 72, 2224 (1998); Inoue et al., J Virol 72, 7024 (1998); WO1998/022607; and WO2005/072364).

Methods of producing pseudotyped AAV vectors are also known (see, e.g., W000/28004), as well as various modifications or formulations of AAV vectors, to reduce their immunogenicity upon in vivo administration (see, e.g., W001/23001; W000/73316; W004/112727; W005/005610; and W099/06562). In some embodiments, AAV vectors may be prepared or derived from various serotypes of AAVs which may be mixed together or mixed with other types of viruses to produce chimeric (e.g., pseudotyped) AAV viruses.

In some embodiments, a method of high-throughput mapping of viral NtAb conformational epitopes can be utilized, which may comprise HP scanning of mutant viral libraries, immunoprecipitation (IP), and/or next-generation sequencing (NGS) technology.

As discussed, NtAb epitope mapping can be used in the development of new vaccines and drugs for the prevention and treatment of infectious diseases. NtAb epitope mapping can also be used for the development of novel gene delivery vectors. Identification of and knowledge regarding NtAb epitopes may help in the genetic engineering of viral components of novel vectors that can evade, or better evade, the host immune response, as the host immune response can be a significant obstacle in effective in vivo gene therapy. In various embodiments, the present disclosure can overcome the limitations of currently available methods for NtAb epitope mapping (e.g., X-ray co-crystallography, cryoelectron microscopy, synthetic peptide array, phage display, etc.) and may effectively identify conformational epitopes of viral antigens in a high-throughput manner.

NtAbs may recognize mostly conformational epitopes as opposed to linear epitopes. X-ray diffraction and cryoelectron microscopic analyses of co-crystallized antigen-antibody complexes can identify conformational NtAb epitopes. However, it may be technically challenging to apply this method to conformational epitope mapping of multiple samples due to its low-throughput, time-intensive, and cost-consuming nature. Synthetic peptide array-based methods can adopt a high-throughput format but they may primarily identify linear epitopes and may be inefficient in identifying conformational epitopes. Phage display approaches have some ability to identify conformational epitopes but may not necessarily be able to present antigens in their native three dimensional protein structures. In contrast, the methods disclosed herein can express epitopes in the context of native tertiary and quaternary structures of viral proteins and identify conformational epitopes of multiple samples at one time in a high-throughput manner.

In various embodiments, the methods disclosed herein can use DNA/RNA-barcoded HP scanning libraries in which platform viral proteins that are not neutralized by NtAbs of interest carry HPs derived from homologous viral proteins that are neutralized by the NtAbs of interest for which one may wish to identify conformational epitopes. HPs can be expressed in the platform viral proteins with appropriately juxtaposed amino acids in native-like tertiary and quaternary structures. Examples of HP scanning libraries include, but are not limited to, the AAV2R585E-HP and AAV9-HP libraries.

Conventional epitope mapping methods such as peptide array- or phage display-based systems can map epitopes of one antigen or one antibody at a time. The methods of the present disclosure can make it possible to map epitopes of multiple antibodies against multiple antigens at one time by an NGS-based method such as, but not limited to, multiplexed ILLUMINA sequencing technology.

In certain embodiments, the present method may comprise the following steps: 1) incubation of samples and a HP scanning library; 2) IP; 3) viral DNA extraction; 4) PCR amplification of viral DNA barcodes; 5) multiplexed ILLUMINA barcode sequencing; and/or 6) data analysis.

An in vitro IP-based AAV Barcode-Seq method can be used to identify anti-AAV antibody epitopes as opposed to the previously reported in vivo approach described above. Also, the highest peak around the amino acid positions 452-457 in the capsid may be a potential dominant epitope for antibodies against various AAV serotypes.

In some embodiments, IP conditions may be optimized using a recombinant AAV9 vector, anti-AAV9 mouse sera, and protein A/G agarose beads. Additionally, a DNA-barcoded AAV HP scanning capsid mutant library comprising 78 AAV clones can be produced, which comprises nineteen AAV2R585E-derived HP mutants and five AAV9-derived HP mutants that span a 14-amino-acid region in and flanking the vicinity of the highest peak of the AAV1, AAV2, AAV7, AAV8, and AAV9 capsids. Using this library, and anti-AAV1, anti-AAV2, anti-AAV7, anti-AAV8, anti-AAV9, and naïve mouse sera collected from four mice per serotype/native, IP can be performed and AAV library genomes from both immunoprecipitates and supernatants may be recovered, which may then be subjected to the AAV Barcode-Seq analysis. Mutants harboring AAV1-, AAV2-, AAV7-, AAV8-, and AAV9-derived peptides spanning eight amino acids within the vicinity of the highest peak, but not other mutants or the control AAV2R585E or AAV9, can be found to be captured by the corresponding anti-AAV serotype sera of some, if not all, of the immunized mice, indicating that the identified peptides constitute a dominant epitope. Thus, a combination of AAV Barcode-Seq with IP can map anti-AAV antibody epitopes in a high-throughput manner.

In some embodiments, a method of identifying one or more dominant epitopes in a viral vector may comprise contacting a mutant capsid of a virus with serum from a subject previously exposed to the virus and immunoprecipitating serum immunoglobulins from the serum. In various embodiments, the viral vector may be an AAV vector. In certain embodiments, the mutant capsid of the virus may be an AAV mutant capsid. In some embodiments, the mutant capsid of the virus of the disclosed method may be included in a mutant capsid library, wherein the capsids in the mutant capsid library are barcoded.

In some embodiments, an AAV1 viral vector may comprise an antibody neutralizing mutation in amino acids 452-457 in the AAV1 capsid (452-QSGSAQ-457) (SEQ ID NO:1). In other embodiments, an AAV9 vector may comprise an antibody neutralizing mutation in amino acids 453-457 in the AAV9 capsid (453-GSGQN-457) (SEQ ID NO: 2). In certain embodiments, the antibody neutralizing mutation of either the AAV1 viral vector or the AAV9 viral vector may comprise a mutation to an alanine.

A dsAAV9-HP-U6-VBCLib-2 HP-scanning mutant capsid library containing a total of 338 AAV clones has been created. These clones are composed of 153 AAV9-HP mutants, AAV2, AAV2R585E and AAV9. The IP-Seq (Immunoprecipitation followed by AAV Barcode-Seq) has been optimized using Protein A/G magnetic beads. An epitope in the AAV2 capsid that is recognized by the mouse monoclonal antibody against intact AAV2 particles (A20) has been mapped by IP-Seq. Epitopes in the AAV2 capsid have been mapped that are recognized by the mouse polyclonal antibodies developed in mice immunized by intravenous injection of an AAV2 vector. Strategies for the creation of anti-AAV neutralizing antibody-escaping AAV capsid mutants have been developed based on the new IP-Seq data.

AAV Barcode-Seq

AAV Barcode-Seq, an NGS-based method that allows the characterization of phenotypes of hundreds of different AAV strains (i.e., naturally occurring serotypes and laboratory-engineered mutants) in a high-throughput manner with significantly reduced time and effort and using only a small number of subjects (e.g., tissue cultures and experimental animals), has recently been established (Adachi K et al., Nat Commun 5, 3075 (2014)). Using this approach, biological aspects including, but not limited to, blood clearance rate, transduction efficiency, tissue tropism, and reactivity to anti-AAV NtAbs can be assessed. FIGS. 1A-1D schematically depict the AAV Barcode-Seq approach. The principle of this approach is as follows. When a library stock comprising many different AAV strains is applied to certain types of samples (e.g., cells), the composition of the AAV population would in theory not change between the original input library and the library recovered from the samples if each of the AAV strains had exactly the same biological properties in a given context. However, if some strains show a different biological property (e.g., faster blood clearance or more efficient cellular internalization) compared to the others, there would be a change in the population composition between the input library (i.e., the library stock) and the output library (i.e., the library recovered from the samples). The basic method consists of a bioinformatic comparison between the input and output libraries using a similar principle as that employed in RNA-Seq (Wang Z et al., Nat Rev Genet 10, 57-63 (2009)). This method allows the quantification of phenotypic differences between different AAV strains as a function of strain demographics. Such an analysis becomes possible by tagging each AAV strain with a unique short DNA barcode and applying ILLUMINA barcode sequencing to the resulting population (Smith AM et al., Genome Res 19, 1836-1842 (2009)).

Figure 2A:
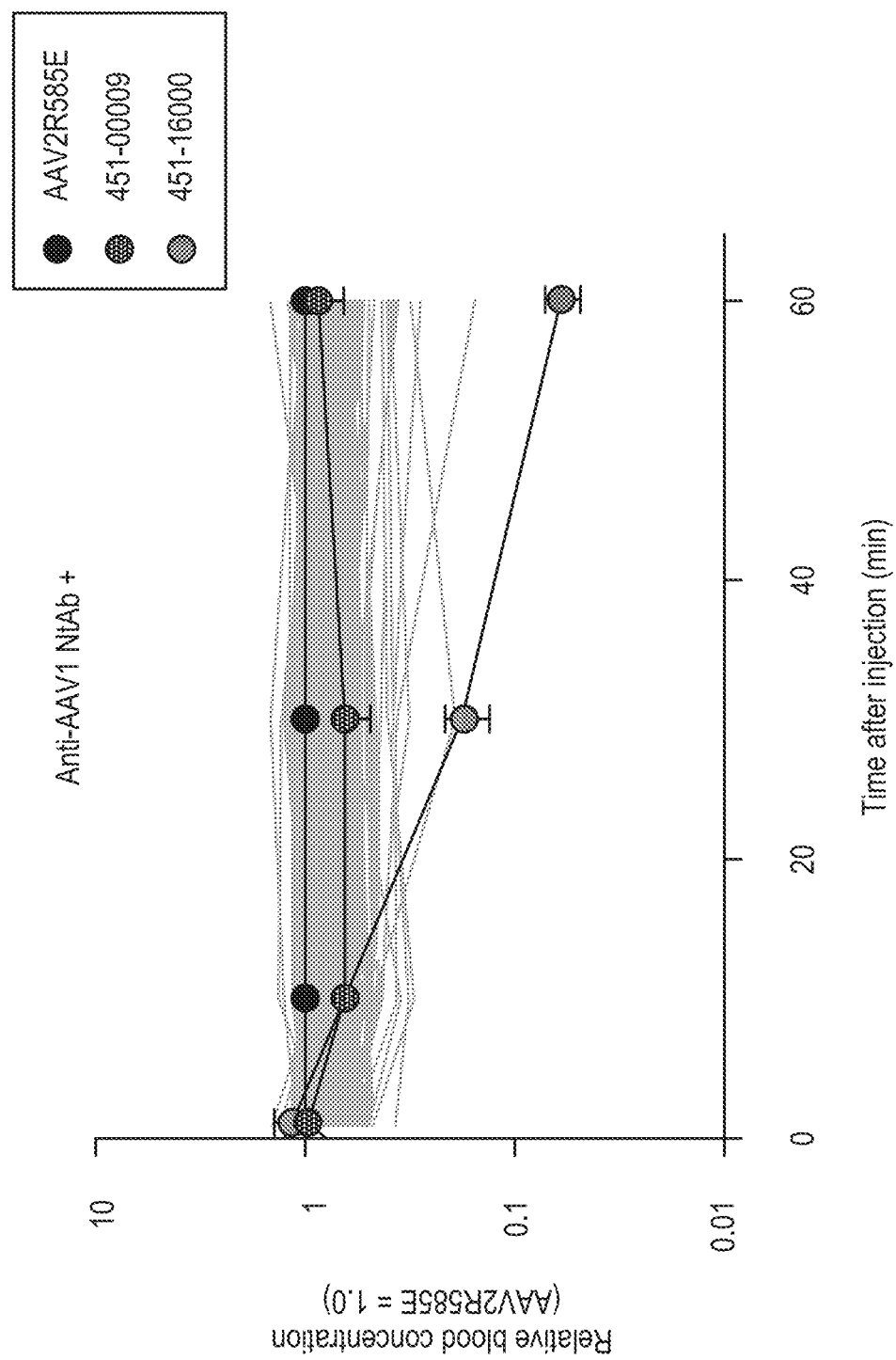
FIG. 2A is a graph showing pharmacokinetic profiles of 117 HP scanning AAV2R585E mutants following intravenous injection of AAV2R585E-HP-VBCLib in anti-AAV1 NtAb-positive mice.
Figure 2B:
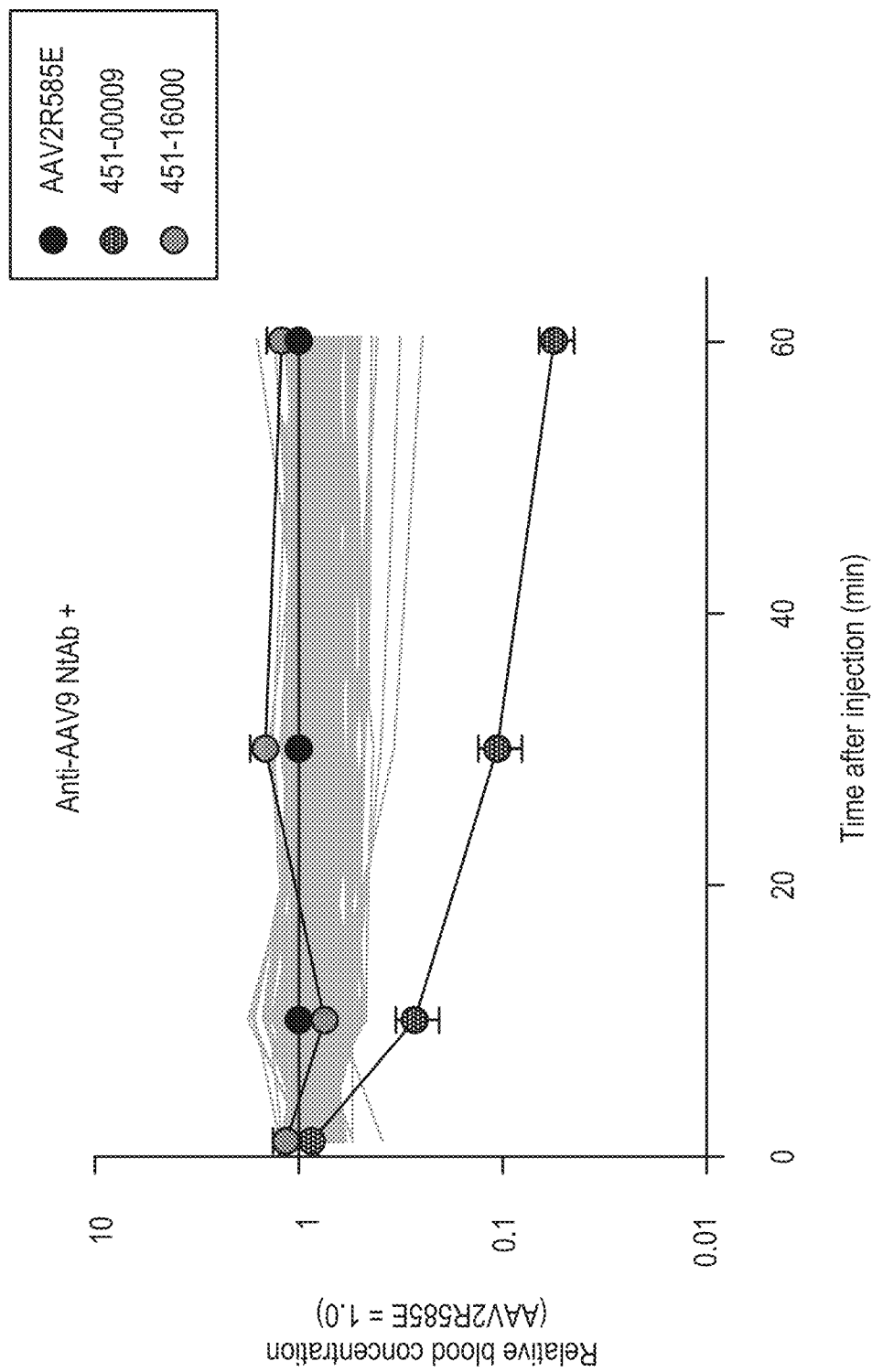
FIG. 2B is a graph showing pharmacokinetic profiles of 117 HP scanning AAV2R585E mutants following intravenous injection of AAV2R585E-HP-VBCLib in anti-AAV9 NtAb-positive mice.
Figure 2C:
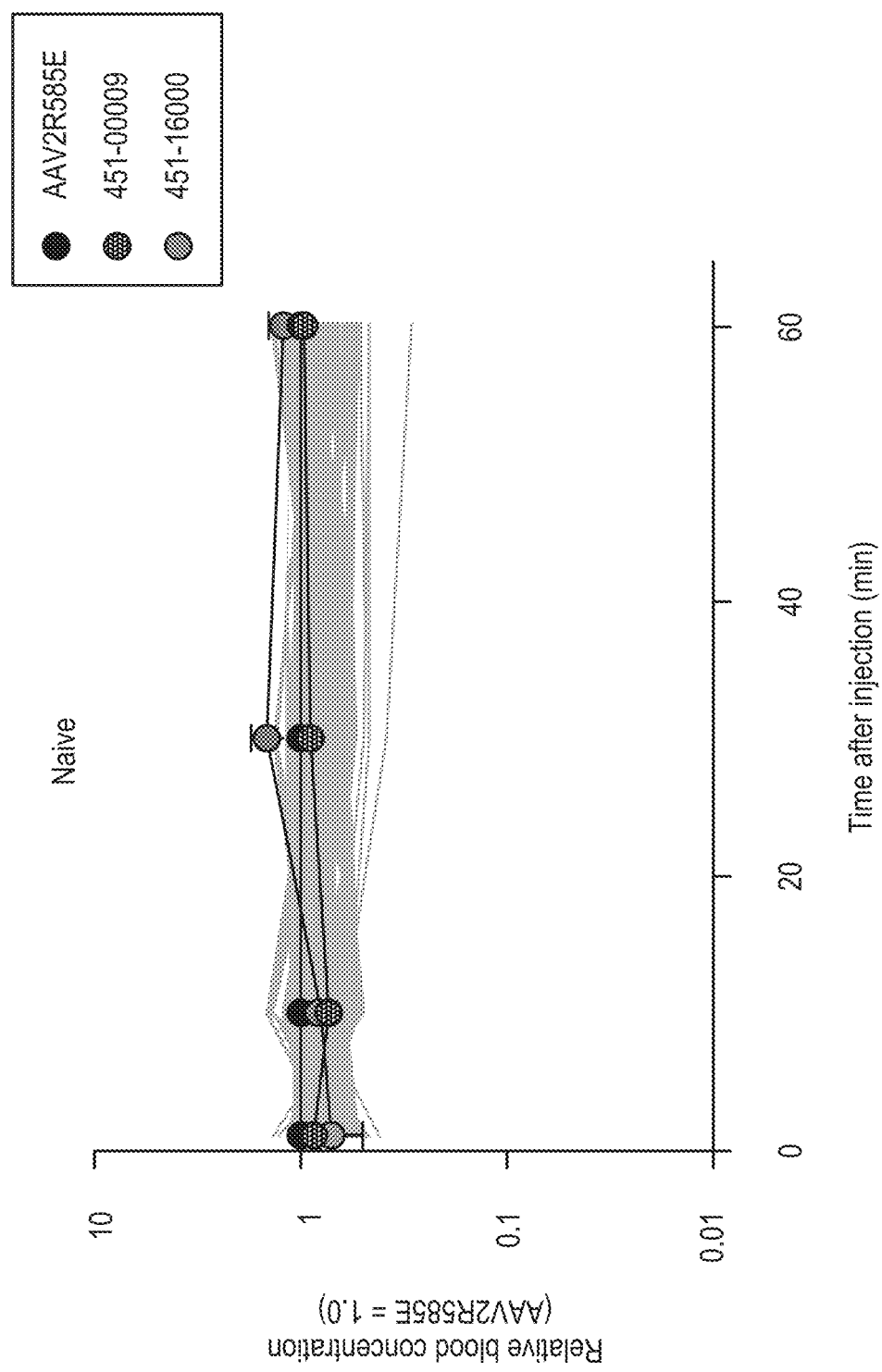
FIG. 2C is a graph showing pharmacokinetic profiles of 117 HP scanning AAV2R585E mutants following intravenous injection of AAV2R585E-HP-VBCLib in naïve mice. For each of FIGS. 2A, 2B, and 2C, blood AAV concentrations of each AAV mutant relative to those of AAV2R585E were determined by AAV Barcode-Seq. Only the results of AAV2R585E, 451-16000, and 451-00009 are highlighted with the patterned lines, as indicated. The results of all the other 115 HP mutants are shown with gray lines. The 451-16000 and 451-00009 exhibited significantly accelerated blood clearance only in anti-AAV1 and anti-AAV9 NtAb-harboring animals, respectively. This was not observed in the naïve animals. In the 451-16000 and 451-00009 mutants, the native AAV2R585E sequence 451-PSGTTT-456 (SEQ ID NO:3) located at the 3-fold spike was replaced with QSGSAQ (AAV1) (SEQ ID NO:1) and GSGQN (AAV9) (SEQ ID NO:2), respectively. This indicates that QSGSAQ (SEQ ID NO:1) and GSGQN (SEQ ID NO: 2) are anti-AAV1 and anti-AAV9 capsid antibody epitopes, respectively.

In Vivo-Based Anti-AAV NtAb Epitope Mapping Using AAV2R585E Hexapeptide Scanning Libraries Construction has been completed of a total of 452 hexapeptide (HP) scanning AAV2R585E capsid mutants that carry all the AAV1-, AAV6-, AAV7-, AAV8-, and AAV9-specific HPs that are not present in the AAV2 capsid (see Table 1). In Adachi K et al., Nat Commun 5, 3075 (2014), AAV2R585E-HP-VBCLib-1 and 2 libraries were produced containing a total of 117 capsid-forming HP mutants, the libraries were injected intravenously into anti-AAV1 or AAV9 NtAb-harboring C57BL/6 mice (n=3) or naive mice (n=2) at $1 \times 10^{13}$ vg/kg, and relative blood concentrations of each mutant were determined at one, 10, 30 and 60 minutes post-injection by AAV Barcode-Seq. Because there is no or minimal serologic cross-reactivity between AAV2 and any of AAV1, AAV6, AAV7, AAV8, and AAV9 (Gao G et al., J Virol 78, 6381-6388 (2004)), only AAV2R585E mutants with a HP containing an antibody epitope would be neutralized, and therefore would be cleared faster than other mutants in the same immunized animal or faster than the same mutant in naïve animals. By taking this approach, 452-QSGSAQ-457 (SEQ ID NO:1) and 453-GSGQN-457 (SEQ ID NO:2) were identified as epitopes for mouse anti-AAV1 and AAV9 NtAbs developed by viral immunization (see FIGS. 2A-2C). Taking the same approach, 449-RTQSNPGGTAG-459 (SEQ ID NO:4) was identified as a mouse anti-AAV7 NtAb epitope. These observations establish that injection of AAV2R585E-HP scanning libraries into anti-AAV NtAb positive mice combined with AAV Barcode-Seq can identify anti-AAV NtAb epitopes effectively.

Figure 3A:
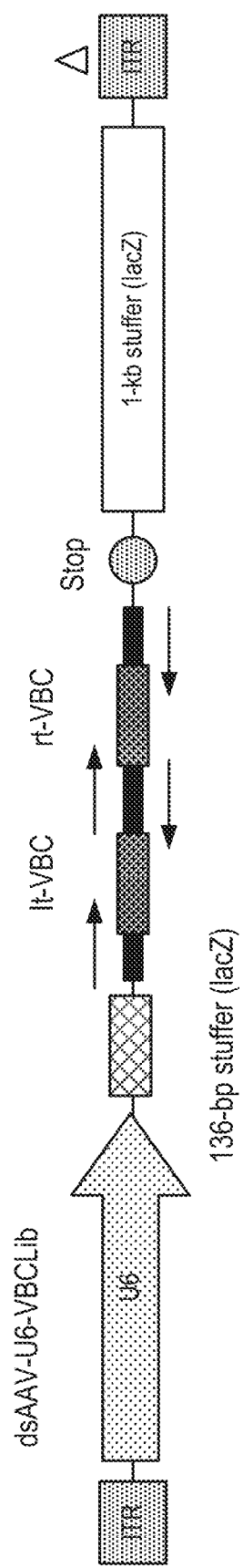
FIG. 3A is a representation of an RNA barcode-expressing recombinant AAV (rAAV). Clone-specific DNA barcodes (lt-VBC and rt-VBC) are transcribed into RNA under the control of the U6 promoter.
Figure 3B:
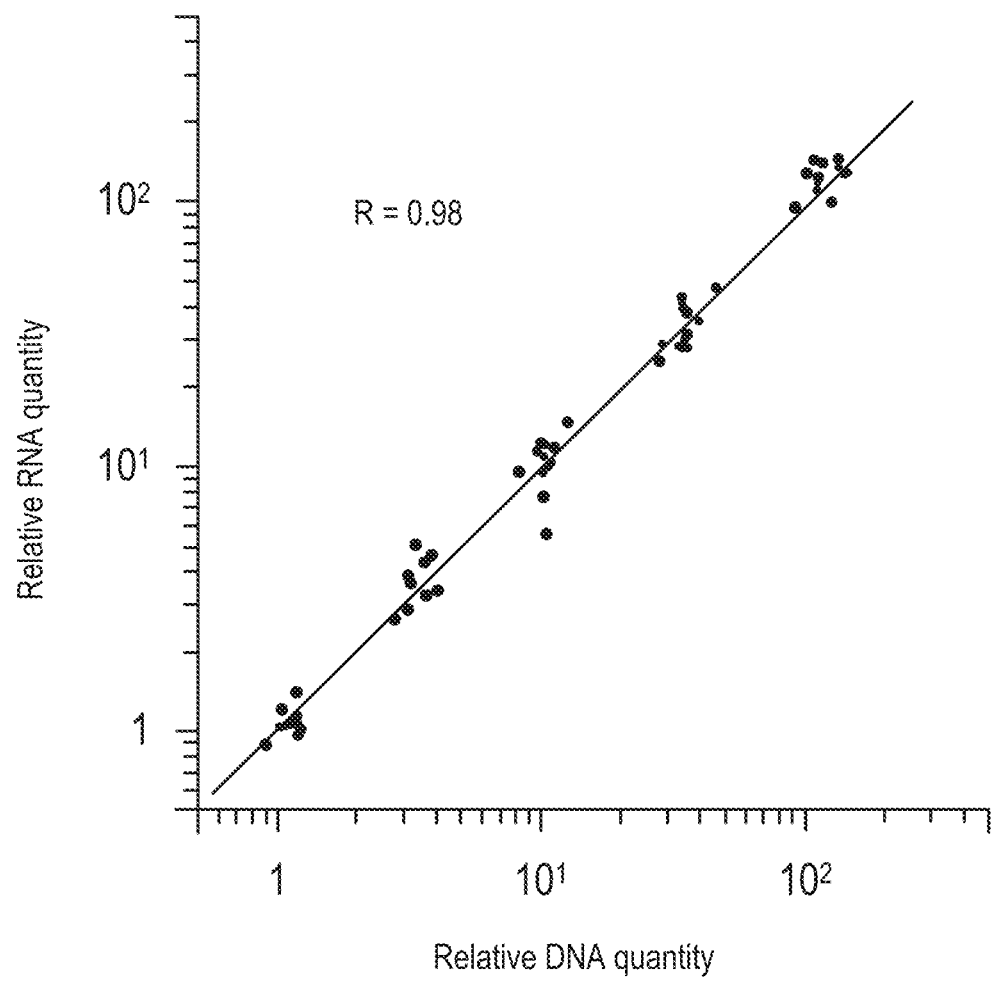
FIG. 3B is a graph depicting a scatter plot showing a linear correlation between relative DNA and RNA quantities determined by AAV DNA/RNA Barcode-Seq. HEK293 cells were infected with two different AAV libraries containing 25 rAAV2 clones mixed at an equal amount or at approximately a 1:3:10:30:100 ratio, and harvested 48 hours post-infection. Each clone was tagged with a clone-specific barcode. Relative DNA and RNA quantifies of each clone in the same HEK293 cell sample were determined by ILLUMINA barcode sequencing read numbers and plotted.

Establishment of a Universal AAV DNA/RNA Barcode-Seq System Expressing RNA Barcodes A universal Barcode-Seq system expressing RNA barcodes, termed AAV DNA/RNA Barcode-Seq, has been devised. In this system, AAV libraries are produced in which each viral particle contains a DNA genome that is devoid of the rep and cap genes but is transcribed into an RNA barcode unique to its own capsid. To show proof-of-principle of this new method, two libraries of 25 recombinant AAV2 viral clones mixed at defined ratios were constructed, HEK293 cells were infected with each library in duplicate, and the cells were harvested at 48 hours post-infection. In these libraries, each viral clone carried the dsAAV-U6-VBCLib genome expressing RNA containing a pair of clone-specific 12 ribonucleotides transcribed from the corresponding DNA barcode sequences placed downstream of the human U6 snRNA promoter (see FIG. 3A). ILLUMINA sequencing of DNA-PCR and reverse-transcription (RT)-PCR barcode amplicons from total DNA and RNA extracted from the same library-infected cells showed that viral genome expression could be determined by Barcode-Seq in at least a 2-log dynamic range with a Pearson's correlation coefficient of 0.98 (see FIG. 3B). This RNA barcode system, AAV DNA/RNA Barcode-Seq, has been employed for anti-AAV NtAb epitope mapping.

Figure 1C:
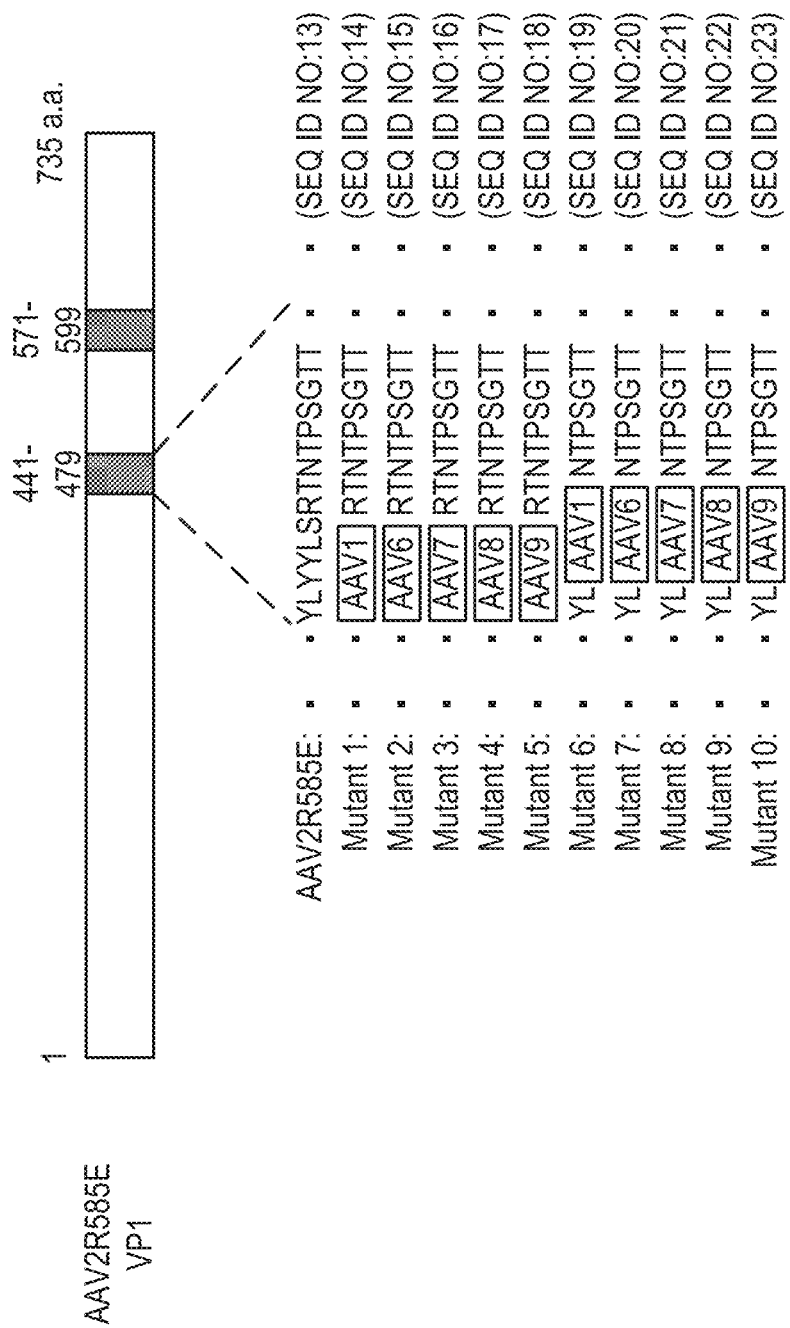
FIG. 1C is a representation of hexapeptide (HP) scanning mutagenesis of the AAV2R585E capsid at a two amino acid interval.

AAV Libraries for Anti-AAV NtAb Epitope Mapping Created Based on the Universal AAV DNA/RNA Barcode-Seq System In this new system, DNA/RNA-barcoded dsAAV-U6-VBCLib libraries packaged with HP scanning mutants can be produced. Such HP mutants can be AAV2R585E-HP scanning mutants for anti-AAVx NtAb epitope mapping (x=any strains other than AAV2 that do not cross-react with anti-AAV2 NtAb) and AAV9-HP scanning mutants for anti-AAV2 NtAb epitope mapping. The structure of AAV2R585E-HP mutants is shown in FIG. 1C. AAV9-HP mutants are those in which AAV9 HPs are replaced with those derived from the AAV2 capsid. All of them are HP scanning libraries that contain the dsAAV-U6-VBCLib genome (see FIG. 3A). DNA/RNA-barcoded dsAAV2R585E-HP-U6-VBCLib libraries for anti-AAV1, anti-AAV6, anti-AAV7, anti-AAV8, and anti-AAV9 NtAb epitope mappings and DNA/RNA-barcoded dsAAV9-HP-U6-VBCLib libraries for anti-AAV2 NtAb epitope mapping can be created. The former set of libraries can comprise a total of 452 AAV2R585E-HP scanning mutants, and the latter set of libraries can comprise 153 AAV9-HP mutants. These mutants, in theory, can cover all the potential hexapeptide epitopes of AAV1, AAV2, AAV6, AAV7, AAV8, and AAV9. Each library will contain two clones per mutant plus 15 clones each of the reference controls, AAV9 and AAV2R585E.

Immunoprecipitation (IP)-Seq Based Anti-AAV Antibody Epitope Mapping

The IP-Seq based method does not require animals and is capable of mapping antibody epitopes of multiple samples at one time using multiplexed ILLUMINA sequencing. Differentiation between NtAb epitopes and non-NtAb epitopes may be achieved by integrating an AAV RNA Barcode-Seq-based neutralization antibody assay into a system as detailed below in the section "AAV RNA Barcode-Seq-based analysis of the neutralizing ability of anti-AAV antibodies with defined epitopes."

The procedure for IP-Seq based anti-AAV antibody epitope mapping can be as follows. First, 25 µl of serum samples (containing anti-AAV NtAbs) and 20 µl of PROTEIN A/G PLUS-AGAROSE (SANTA CRUZ sc-2003) can be incubated in a total volume of 100 µl in PBS in 1.5 ml tubes at 4° C. for 1 hour on a rotation device. After washing with PBS, a DNA/RNA-barcoded dsAAV-U6-VBCLib library and the agarose beads coated with immunoglobulins can be mixed in a total volume of 100 µl PBS, and may then be incubated at 4° C. overnight on a rotation device. On the next day, a standard IP procedure may be followed, the supernatants and immunoprecipitates can be collected, and viral genome DNA can be extracted using a WAKO DNA Extraction Kit following Proteinase K treatment of the samples. The subsequent procedure may be similar to that used for AAV Barcode-Seq as described in Adachi K et al., Nat Commun 5, 3075 (2014). Briefly, left and right viral clone-specific barcodes (lt-VBC and rt-VBC in FIGS. 1A-1D) may be PCR-amplified using viral genome DNA recovered from the IP supernatants and precipitates. The PCR primers can be indexed with sample-specific DNA barcodes. All the PCR amplicons may then be mixed into a pool and the pool may be subjected to ILLUMINA sequencing. The ILLUMINA sequencing data may be bioinformatically analyzed to detect demographic changes of the AAV library in each sample. The principle of the method is that viral clones with higher avidity to sample immunoglobulins than others can be detected as clones that are decreased or depleted in the supernatants while enriched in the precipitates by ILLUMINA barcode sequencing. Such clones may likely carry epitopes for anti-AAV antibodies under investigation, and the epitopes targeted by the antibodies may likely be the heterologous peptides incorporated into the capsid of particular AAV clones showing a demographic change. $1 \times 10^7$, $1 \times 10^8$, and $1 \times 10^9$ vg per 1.5 ml tube have been used and it has been found that this range of the virus quantity may give clear results as described below.

To show proof-of-principle, a DNA/RNA-barcoded dsAAV-U6-VBCLib-1 library exhibiting low diversity was produced. This library was designed to identify anti-AAV1, AAV2, AAV6, AAV7, AAV8, and AAV9 antibody epitopes at the highest peak around the amino acid positions 452-457 in the capsid. Based on data obtained in the in vivo-based epitope mapping study as described above, it was hypothesized that this region is a potential dominant epitope for antibodies against various AAV serotypes. Therefore, it was assumed that targeting this region in the proof-of-principle experiments may have a higher success rate in finding anti-AAV antibody epitopes for various AAV serotypes. This library was composed of 78 AAV clones, which included 19 AAV2R585E-derived HP mutants and five AAV9-derived HP mutants that spanned a 14-amino-acid region in and flanking the vicinity of the highest peak of the AAV1, AAV2, AAV7, AAV8, and AAV9 capsids (see FIG. 4) in addition to 15 clones each of reference control AAV strains, AAV9, and AAV2R585E devoid of HP mutations. Using this library and anti-AAV1, anti-AAV2, anti-AAV7, anti-AAV8, anti-AAV9 mouse sera collected from 3-4 mice per serotype, the IP-Seq-based epitope mapping procedure described above was performed. The mice from which anti-AAV sera was collected had been immunized by intravenous injection of $1 \times 10^{11}$ vg of AAV-CMV-lacZ vector packaged with the corresponding serotype capsids. The data presented below were obtained when $1 \times 10^9$ vg per tube was used for IP-Seq. The IP-Seq procedure was also performed using native mouse sera to control nonspecific binding of the AAV library to the immunoglobulin-coated agarose beads.

Figure 5A:
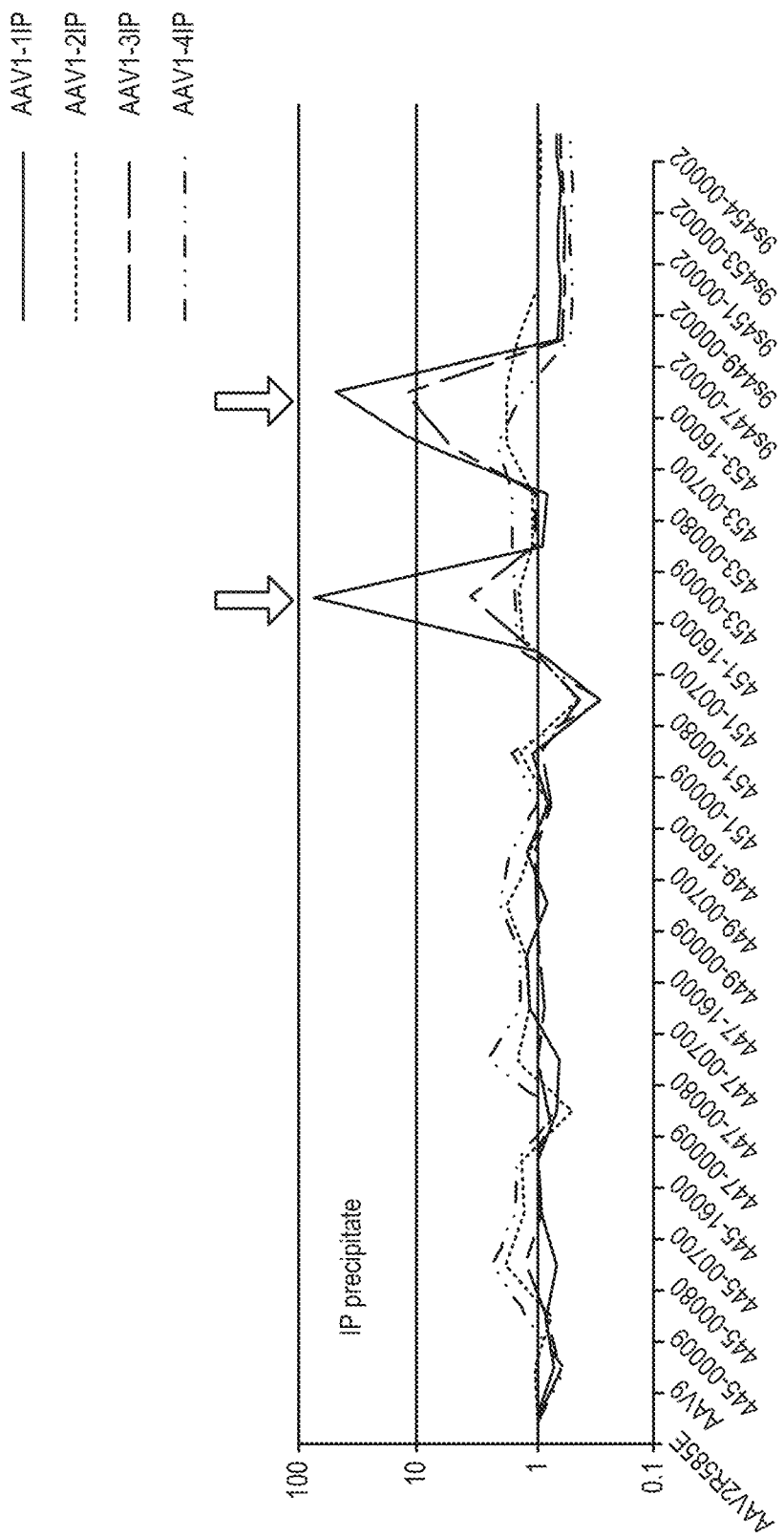
FIG. 5A is a graph plotting the averages of the relative quantities of two different clones carrying the same HP mutation in an IP precipitate.
Figure 5B:
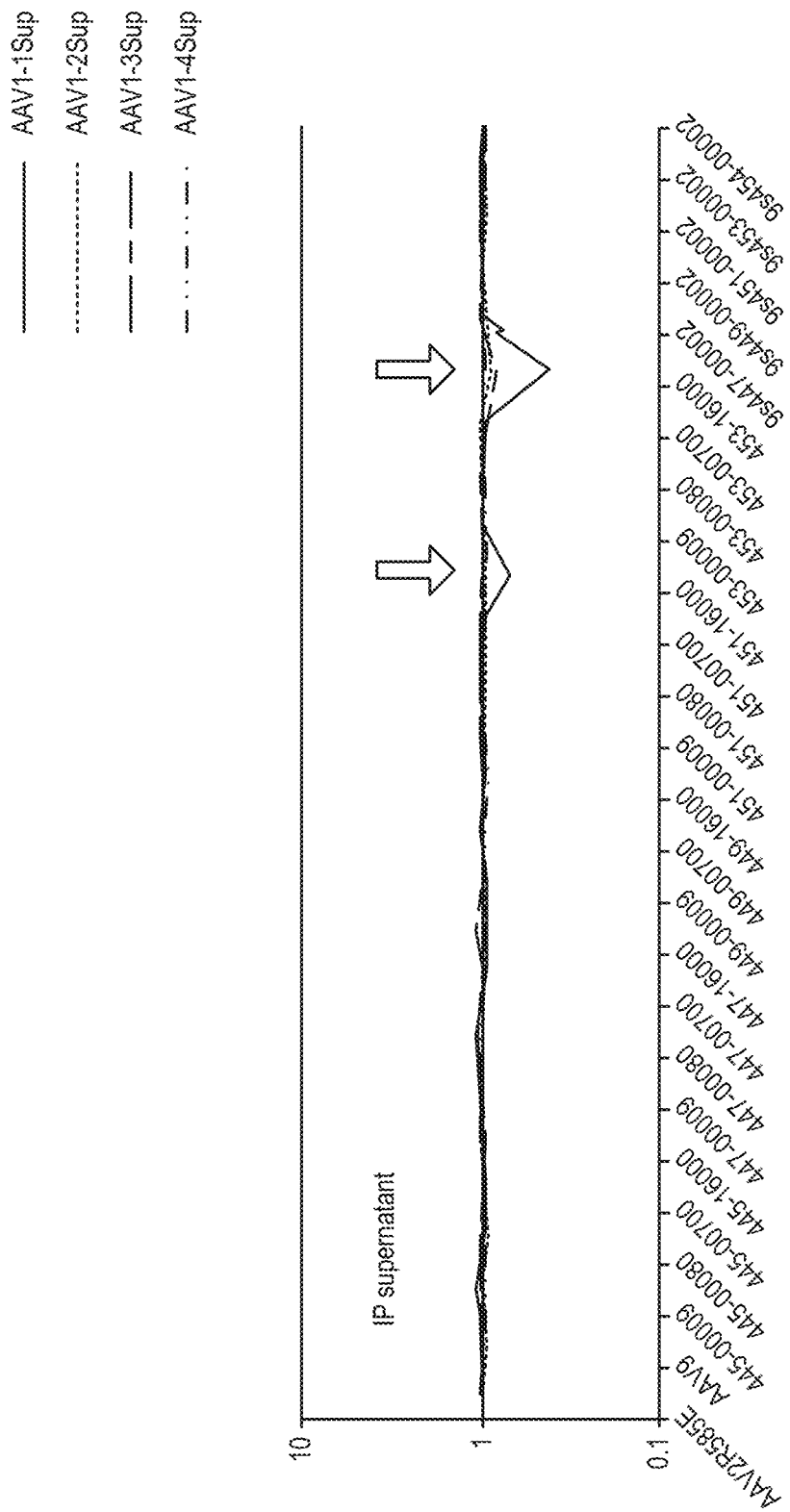
FIG. 5B is a graph plotting the averages of the relative quantities of two different clones carrying the same HP mutation in an IP supernatant. For each of FIGS. 5A and 5B, four 8-week-old C57BL/6 male mice (Mouse 1, 2, 3 and 4) were injected intravenously with AAV1-CMV-lacZ vector at a dose of $1 \times 10^{11}$ vector genomes (vg) per mouse. Serum samples containing anti-AAV1 NtAbs were collected 3 weeks post-injection. 20 µl of PROTEIN A/G PLUS-AGAROSE beads were first coated with sample immunoglobulins by incubating the beads with 25 µl of serum samples at 4° C. for one hour, and then reacted with $1 \times 10^{9}$ vg of DNA/RNA-barcoded dsAAV-U6-VBC-Lib-1 at 4° C. overnight. This library contained 72 AAV clones composed of 24 HP mutants and two reference controls (AAV2R585E and wild-type AAV9, 15 clones each). Viral genomic DNAs were extracted from agarose beads-bound and unbound AAV particles in the IP precipitates and the IP supernatants, respectively, and subjected to the AAV Barcode-Seq analysis (id.). The relative quantity of each clone (two clones per mutant) determined by ILLUMINA sequencing read numbers was normalized with the ILLUMINA sequencing read numbers of the reference control AAV2R585E. The Y-axis shows Phenotypic Difference (PD) values (id.) of each mutant relative to the control AAV2R585E in antibody-positive sera, normalized with PD values obtained with naïve mouse serum. Plotted are the averages of the relative quantities of two different clones carrying the same HP mutation. Arrows indicate mutants harboring the heterologous peptides that bind to anti-AAV1 antibody, and therefore, represent anti-AAV1 antibody epitopes.

FIGS. 5A and 5B show the results of IP-Seq using anti-AAV1 mouse sera collected from four mice. Mouse 1 exhibited >10 fold enrichment of 451-16000 and 453-16000 in the IP precipitations, and Mouse 3 also showed >10 fold enrichment of 453-16000 in the IP precipitation. Consistent with this observation, reduction of 451-16000 and 453-16000 in the supernatant, although not dramatic, was found in the Mouse 1 serum. Mouse 2 and Mouse 4 exhibited a lesser degree of enrichment of 453-16000 in the precipitation. The reduction of these mutants in the supernatants was not detected in the Mouse 2, 3, and 4 sera. These observations indicate that, in Mouse 1 and 3 and perhaps Mouse 2 and 4, an anti-AAV1 antibody epitope resides within the heterologous peptides contained in 451-16000 and 453-16000 (i.e., 452-QSGSAQNK-459 (SEQ ID NO:5)). The fact that the heterologous peptides in these mutants are derived from the AAV1 capsid may also lend support to this conclusion. In addition, this conforms to the result obtained by the in vivo-based epitope mapping by AAV Barcode-Seq (Adachi K et al., Nat Commun 5, 3075 (2014)). The sensitivity of IP-Seq may be increased by decreasing the amount of AAV library added to the IP reaction. For example, the use of $1 \times 10^7$ vg or $1 \times 10^8$ vg per tube may identify epitopes more effectively and clearly in both the IP supernatants and the IP precipitations. A preliminary experiment using $1 \times 10^7$ vg and $1 \times 10^8$ vg per tube of an AAV library has supported this prediction.

Figure 6:
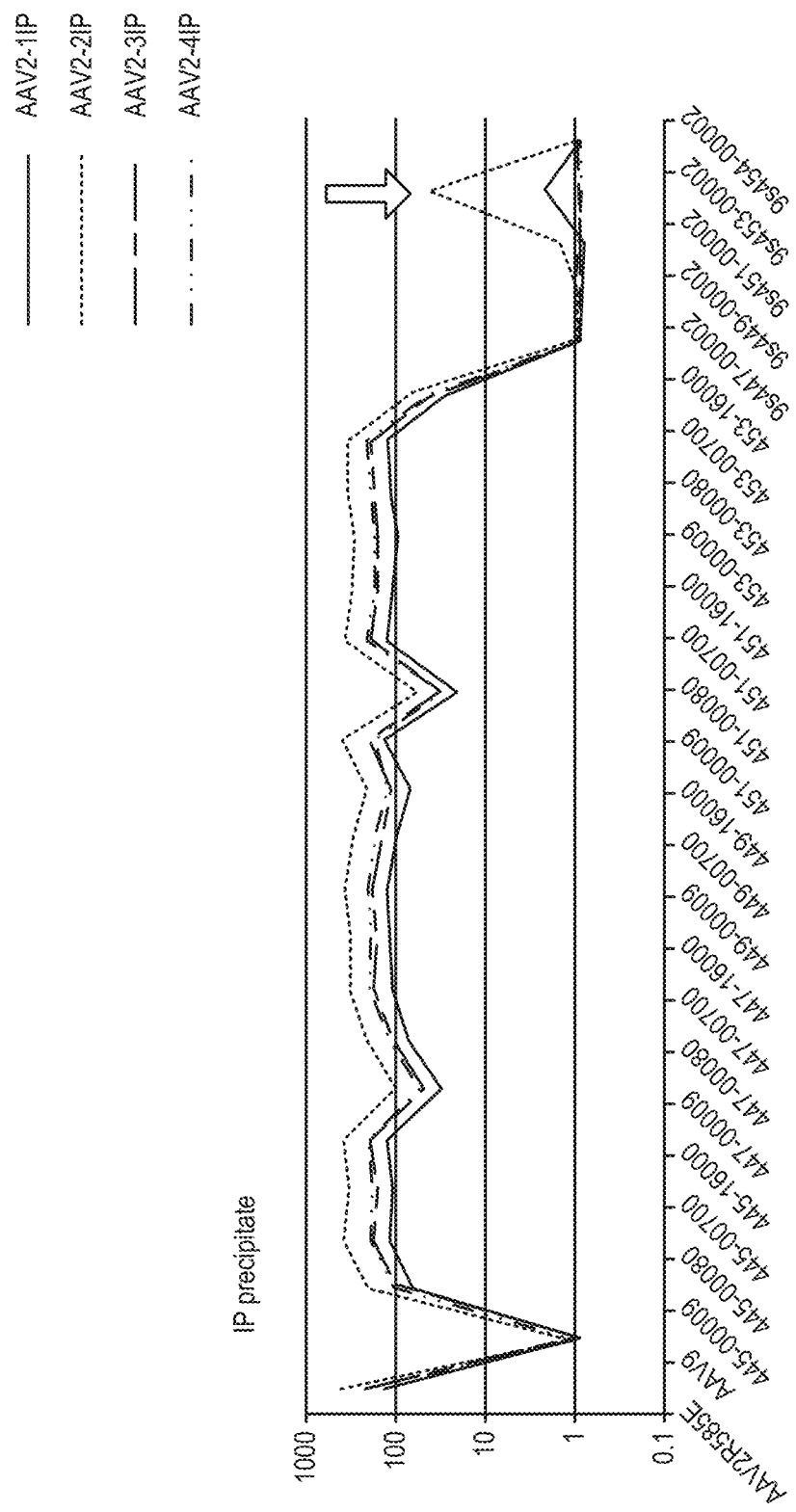
FIG. 6 is a graph wherein the Y-axis shows Phenotypic Difference (PD) values (id.) of each mutant relative to the control wild-type AAV9. An arrow indicates a mutant harboring the heterologous peptide that binds to anti-AAV2 antibody, and therefore, represents an anti-AAV2 antibody epitope. Four 8-week-old C57BL/6 male mice (Mouse 1, 2, 3 and 4) were injected intravenously with AAV2-CMV-lacZ vector at a dose of $1 \times 10^{11}$ vg/mouse. Serum samples containing anti-AAV2 NtAbs were collected three weeks post-injection. The subsequent experimental procedure is the same as that for FIGS. 5A and 5B.

FIG. 6 shows the results of IP-Seq using anti-AAV2 mouse sera collected from four mice. All the AAV2R585E mutants were found enriched in the IP precipitations. In Mouse 2, 453-00002 was enriched by >10 fold in the precipitates, demonstrating that the AAV2-derived heterologous peptide in this mutant, 451-PSGTTT-456 (SEQ ID NO:3), may be an epitope for anti-AAV2 antibodies developed in Mouse 2.

Figure 7:
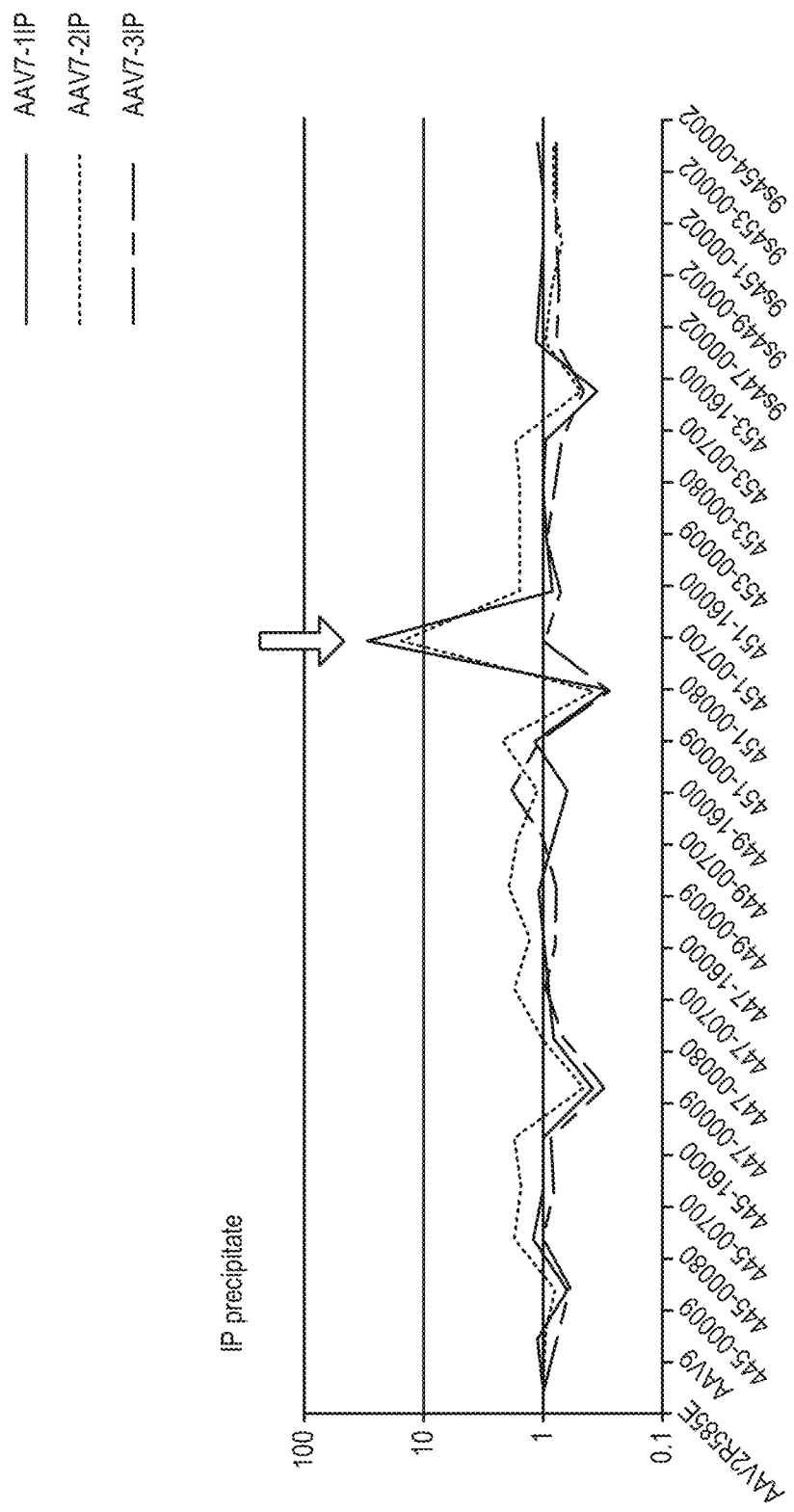
FIG. 7 is a graph wherein the Y-axis shows Phenotypic Difference (PD) values (id.) of each mutant relative to the control AAV2R585E. An arrow indicates a mutant harboring the heterologous peptide that binds to anti-AAV7 antibody, and therefore, represents an anti-AAV7 antibody epitope. Three 8-week-old C57BL/6 male mice (Mouse 1, 2, and 3) were injected intravenously with AAV7-CMV-lacZ vector at a dose of $1 \times 10^{11}$ vg/mouse. Serum samples containing anti-AAV7 NtAbs were collected three weeks post-injection. The subsequent experimental procedure is the same as that for FIGS. 5A and 5B.

FIG. 7 shows the results of IP-Seq using anti-AAV7 mouse sera collected from three mice. 451-00700 was significantly enriched in the IP precipitates in Mouse 1 and 2. This demonstrates that AAV7-derived heterologous peptide in the 451-00700 mutant, 453-NPGGTAG-459 (SEQ ID NO:6), may be an epitope for anti-AAV7 antibodies developed in Mouse 1 and 2.

Figure 8:
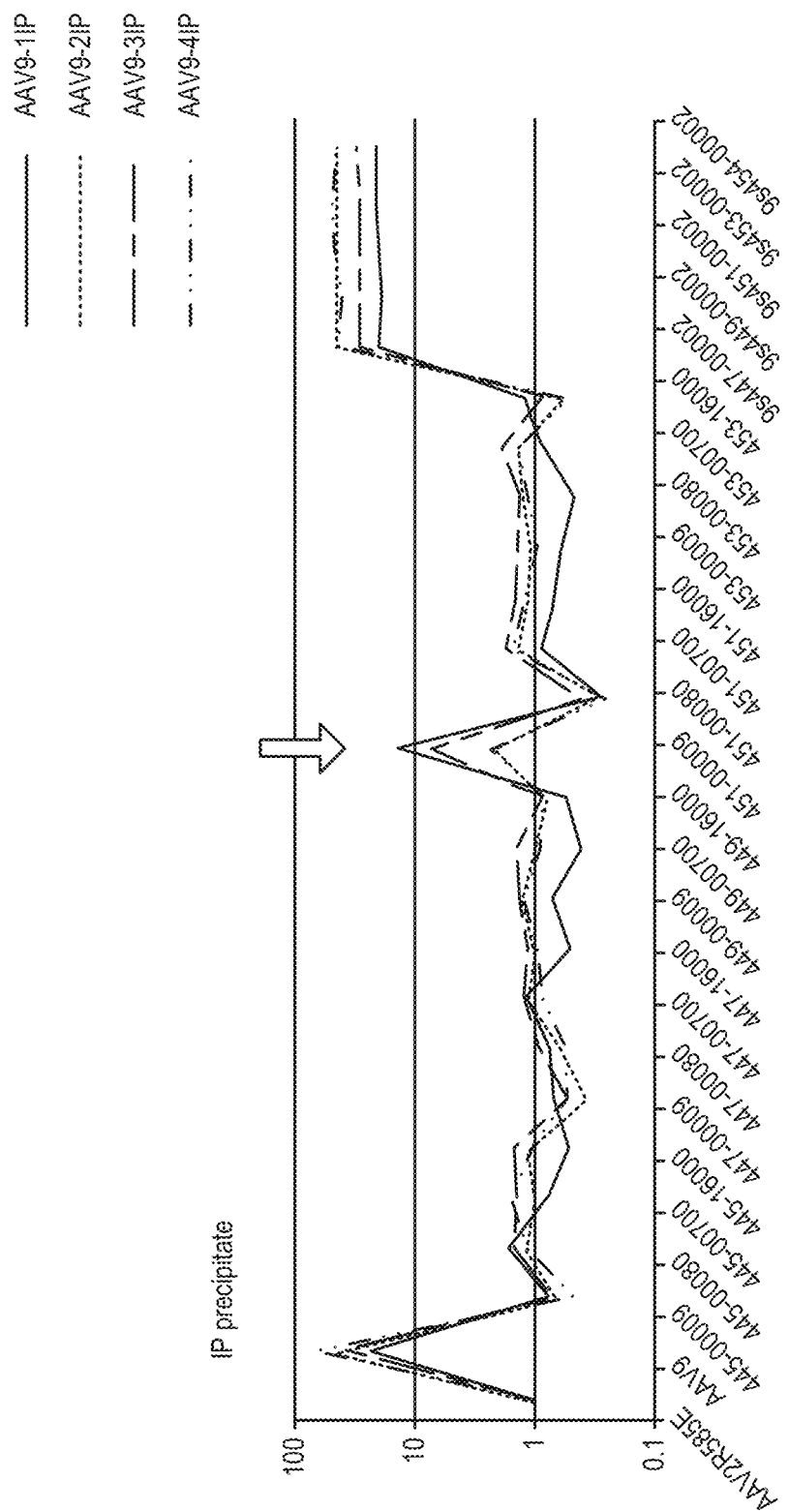
FIG. 8 is a graph wherein the Y-axis shows Phenotypic Difference (PD) values (id.) of each mutant relative to the control AAV2R585E. An arrow indicates a mutant harboring the heterologous peptide that binds to anti-AAV9 antibody, and therefore, represents an anti-AAV9 antibody epitope. Four 8-week-old C57BL/6 male mice (Mouse 1, 2, 3 and 4) were injected intravenously with AAV9-CMV-lacZ vector at a dose of $1 \times 10^{11}$ vg/mouse. Serum samples containing anti-AAV9 NtAbs were collected three weeks post-injection. The subsequent experimental procedure is the same as that for FIGS. 5A and 5B.

FIG. 8 shows the results of IP-Seq using anti-AAV9 mouse sera collected from four mice. 451-00009 was significantly enriched in the IP precipitates in Mouse 1 and 3. This demonstrates that AAV9-derived heterologous peptide in the 451-00009 mutant, 453-GSGQN-457 (SEQ ID NO:2), may be an epitope for anti-AAV9 antibodies developed in Mouse 1 and 3. This also conforms to the result obtained by the in vivo-based epitope mapping by AAV Barcode-Seq (Adachi K et al., Nat Commun 5, 3075 (2014)). Regarding the IP-Seq analysis of anti-AAV8 mouse sera, no epitopes could be detected at the sensitivity of the assay used.

In summary, a series of proof-of-concept experiments demonstrates that the IP-Seq using AAV capsid hexapeptide scanning libraries is a means to map anti-AAV antibody epitopes, presumably including conformational epitopes, effectively and in a high-throughput manner. Although the AAV library used for this preliminary set of experiments contained only 24 hexapeptide (HP) scanning mutants, 452

AAV2R585E-HP mutants were created to look for anti-AAV1, anti-AAV6, anti-AAV7, anti-AAV8, and anti-AAV9 antibody epitopes. A total of 153 AAV9-HP mutants to cover the entire region of AAV2 VP1 capsid protein can also be created. Additionally, the same approach can be exploited for epitope mapping of antibodies against other AAV serotypes or capsid-engineered mutants. This method should also have a potential to be adapted to antiviral antibody epitope mapping for any viruses other than AAV.

AAV RNA Barcode-Seq-Based Analysis of the Neutralizing Ability of Anti-AAV Antibodies with Defined Epitopes AAV DNA/RNA Barcode-Seq may be used to assess the neutralizing ability of anti-AAV antibodies that recognize defined epitopes. The principle of this new assay system is as follows. A DNA/RNA-barcoded dsAAV-U6-VBCLib library that has been prepared for IP-Seq can be pre-incubated with samples under investigation (serum samples, purified monoclonal/polyclonal antibodies, etc.) at 37° C. for one hour or pre-incubated with a naive animal serum devoid of anti-AAV NtAbs (e.g., naïve mouse serum) as a control. The mixture can then be applied to a reporter cell line in vitro in duplicate or in triplicate. Two to three days after AAV library infection, total RNA can be recovered from cells and reverse-transcribed using an AAV genome-specific RT primer. Then clone-specific viral RNA barcodes may be PCR-amplified and subjected to AAV Barcode-Seq (i.e., multiplexed ILLUMINA barcode sequencing followed by data analysis). When the ILLUMINA sequencing data are compared between the samples and the control, AAV clones that are neutralized by anti-AAV antibodies can be identified as a relative decrease of ILLUMINA sequencing reads among all the AAV clones in the library used for the analysis. By combining the heterologous peptide information of each AAV clone and the AAV Barcode-Seq results, it may be determinable whether or not an anti-AAV antibody, or anti-AAV antibodies, that recognizes a defined antibody epitope on the capsid can neutralize the virus and impair the virus infectivity. This assay complements IP-Seq because IP-Seq by itself may not be able to differentiate NtAb epitopes from non-neutralizing antibody epitopes, although the in vivo-based epitope mapping approach is capable of differentiation between these two types of anti-AAV antibodies. The reporter cells should be selected carefully because in vitro transduction efficiencies significantly vary depending on cell types and AAV strains. For example, HEK293 cells can be appropriate for anti-AAV2 antibody epitopes and Chinese Hamster Ovary (CHO) Lec2 cells can be appropriate for anti-AAV9 antibody epitopes.

TABLE 1

Hexapeptide scanning AAV2R585E-derived mutants

| Name of mutant[1] | Amino acid substitutions in addition to R585E |
|---|---|
| 441-00700 | S446A |
| 441-16000 | S446N |
| 443-00009 | R447K |
| 445-00009 | R447K/N449I/T450N |
| 445-00080 | N449Q |
| 445-00700 | S446A/N449Q/T450S |
| 445-16000 | S446N/N449Q/T450N |
| 447-00009 | R447K/N449I/T450N/P451G/S452 |
| 447-00080 | N449Q/P451T/S452G |
| 447-00700 | N449Q/T450S/P451N/S452G |
| 447-16000 | N449Q/T450N/P451Q |
| 449-00009 | N449I/T450N/P451G/S452/G453S/T454G |
| 449-00700 | N449Q/T450S/P451N/S452G |
| 449-16000 | N449Q/T450N/P451Q/T454S |
| 451-00009 | P451G/S452/G453S/T454G/T455Q/T456N |
| 451-00080 | P451T/S452G/T455A/T456N |
| 451-00700 | P451N/S452G/T455A/T456G |
| 451-16000 | P451Q/T454S/T455A/T456Q |
| 453-00009 | G453S/T454G/T455Q/T456N/S458Q |
| 453-00080 | T455A/T456N/Q457T/S458Q |
| 453-00700 | T455A/T456G/Q457N/S458R |
| 453-16000 | T454S/T455A/T456Q/Q457N/S458K |
| 455-00009 | T455Q/T456N/S458Q/R459T |
| 455-00080 | T455A/T456N/Q457T/S458Q/R459T |
| 455-00700 | T455A/T456G/Q457N/S458R/R459E |
| 455-16000 | T455A/T456Q/Q457N/S458K/R459D |
| 457-00009 | S458Q/R459T/Q461K |
| 457-00080 | Q457T/S458Q/R459T/Q461G |
| 457-00700 | Q457N/S458R/R459E |
| 457-16000 | Q457N/S458K/R459D/Q461L |
| 459-00009 | R459T/Q461K/Q464V |
| 459-00080 | R459T/Q461G |
| 459-00700 | R459E/S463Y |
| 459-16000 | R459D/Q461L/Q464R |
| 461-00009 | Q461K/Q464V |
| 461-00080 | Q461G/A465G |
| 461-00700 | S463Y/A465G |
| 461-16000 | Q461L/Q464R/A465G/G466S |
| 463-00009 | Q464V/A467P |
| 463-00080 | A465G/A467P/S468N |
| 463-00700 | S463Y/A465G/A467P |
| 463-16000 | Q464R/A465G/G466S/A467P/S468A |
| 465-00009 (R585E.9-4[2]) | A467P/D469N/I470M |
| 465-00080 | A465G/A467P/S468N/D469T/I470M |
| 465-00700 | A465G/A467P/D469T/I470M |
| 465-16000 | A465G/G466S/A467P/S468A/D469G/I470M |
| 467-00009 (R585E.9-5[2]) | A467P/D469N/I470M/R471A/D472V |
| 467-00080 | A467P/S468N/D469T/I470M/R471A/D472N |
| 467-00700 | A467P/D469T/I470M/R471A/D472E |
| 467-16000 | A467P/S468A/D469G/I470M/R471S/D472V |
| 469-00009 | D469N/I470M/R471A/D472V/S474G |
| 469-00080 | D469T/I470M/R471A/D472N/S474A |
| 469-00700 | D469T/I470M/R471A/D472E/S474A |
| 469-16000 | D469G/I470M/R471S/D472V/S474P |
| 471-00009 | R471A/D472V/S474G |
| 471-00080 | R471A/D472N/S474A/R475K |
| 471-00700 | R471A/D472E/S474A/R475K |
| 471-16000 | R471S/D472V/S474P/R475K |
| 473-00009 | S474G/W477Y/L478I |
| 473-00780 | S474A/R475K |
| 473-16000 | S474P/R475K |
| 475-00009 | W477Y/L478I |
| 475-16780 | R475K |
| 477-00009 | W477Y/L478I/C482S |
| 479-00009 | C482S |
| 479-00700 | Y483F |
| 571-00009 | Q575S |
| 571-00780 | Q575E |
| 571-16000 | Q575R/Y576F |
| 573-00009 | Q575S/S578Q |
| 573-00780 | Q575E/S578I |
| 573-16000 | Q575R/Y576F/S578T |
| 575-00009 | Q575S/S578Q/S580A |
| 575-00080 | Q575E/S578I/S580A |
| 575-16000 | Q575R/Y576F/S578T/S580A |
| 577-00009 | S578Q/S580A |
| 577-00080 | S578I/S580A/T581D |
| 577-00700 | S578I/T581S |
| 577-16000 | S578T/S580A/T581V |
| 579-00009 | S580A/L583H |
| 579-00080 | S580A/T581D |
| 579-00700 | T581S |
| 579-06000 | S580A/T581V |
| 579-10000 | S580A/T581V/L583F |
| 581-00009 | L583H/E585S/G586A |
| 581-00080 | T581D/E585Q/G586Q |
| 581-00700 | T581S/E585A/G586A |

TABLE 1-continued Hexapeptide scanning AAV2R585E-derived mutants

| Name of mutant[1] | Amino acid substitutions in addition to R585E |
|---|---|
| 581-06000 | T581V/E585S/G586S |
| 581-10000 | T581V/L583F/E585S/G586S |
| 583-00009 | L583H/E585S/G586A/N587Q/R588A |
| 583-00080 | E585Q/G586Q/R588T |
| 583-00700 | E585A/G586A/R588T |
| 583-06000 | E585S/G586S/N587S/R588T |
| 583-10000 | L583F/E585S/G586S/N587S/R588T |
| 585-00009 (2i9[3]) | E585S/G586A/N587Q/R588A |
| 585-00080 (2i8[3]) | E585Q/G586Q/R588T/Q589A/A590P |
| 585-00700 (2i7[3]) | E585A/G586A/R588T/Q589A |
| 585-16000 (2i1[3]) | E585S/G586S/N587S/R588T/Q589D/A590P |
| 587-00009 | N587Q/R588A/A591Q |
| 587-00080 | R588T/Q589A/A590P/A591Q/T592I |
| 587-00700 | R588T/Q589A/A591Q |
| 587-16000 | N587S/R588T/Q589D/A590P |
| 589-00009 | A591Q/A593G/D594W |
| 589-00080 | Q589A/A590P/A591Q/T592I/A593G/D594T |
| 589-00700 | Q589A/A591Q/A593Q/D594V |
| 589-16000 | Q589D/A590P/A593G |
| 591-00009 | A591Q/A593G/D594W/N596Q |
| 591-00080 | A591Q/T592I/A593G/D594T |
| 591-00700 | A591Q/A593Q/D594V |
| 591-16000 | A593G/N596H |
| 593-00009 | A593G/D594W/N596Q/T597N |
| 593-00080 | A593G/D594T/T597S |
| 593-00700 | A593Q/D594V/T597N |
| 593-06000 | A593G/N596H/T597V/Q598M |
| 593-10000 | A593G/N596H/T597A/Q598M |
| 595-00009 | N596Q/T597N/V600I |
| 595-00080 | T597S/V600A |
| 595-00700 | T597N/V600A |
| 595-06000 | N596H/T597V/Q598M/V600A |
| 595-10000 | N596H/T597A/Q598M/V600A |
| 597-00009 | T597N/V600I |
| 597-06000 | T597V/Q598M/V600A |
| 597-10000 | T597A/Q598M/V600A |
| 599-00009 | V600I |
| 599-16780 | V600A |
| 485-00089 | K490T |
| 487-00080 | K490T/S492T |
| 487-16000 | S492K |
| 491-00009 | S492V/A493T/D494Q |
| 491-00080 | S492T/A493G/D494Q |
| 493-00009 | A493T/D494Q |
| 493-00080 | A493G/D494Q |
| 493-00700 | A493D/D494Q |
| 493-16000 | A493T |
| 495-16780 | E499N/Y500F |
| 497-00009 | Y500F/S501A |
| 497-16000 | E499N/Y500F/S501T |
| 499-00009 | Y500F/S501A/T503P |
| 501-00009 | S501A/T503P/T506S |
| 501-00080 | S501A/G504A/A505G |
| 503-00080 | G504A/A505G |
| 503-16000 | T506S |
| 505-00080 | A505G |
| 505-16000 | T506S/H509N |
| 507-16000 | H509N |
| 509-00780 | D514N |
| 509-16000 | H509N/D514E |
| 513-16000 | D514E/L516I/V517I |
| 515-00080 | V517A |
| 523-00009 | D528E |
| 523-00780 | S525T |
| 525-00009 | D528E/D529G |
| 525-06000 | E530K |
| 527-00009 | D528E/D529G/E531D/K532R |
| 527-00080 | K532R |
| 527-00700 | E531D/K532R |
| 527-06000 | E530K/E531D |
| 527-10000 | E531D |
| 529-00009 | D529G/E531D/K532R |
| 531-00080 | K532R/Q536S |
| 533-00009 | Q536L |
| 533-00700 | Q536S |
| 533-16000 | Q536M |

TABLE 1-continued

Hexapeptide scanning AAV2R585E-derived mutants

| Name of mutant[1] | Amino acid substitutions in addition to R585E |
|---|---|
| 535-16000 | Q536M/L540M |
| 537-16000 | L540M |
| 543-00009 | S547T/E548G |
| 543-00080 | G546N/S547A/E548A |
| 543-00700 | Q545T/S547A/E548T |
| 543-16000 | Q545E/G546S/S547A/E548G |
| 545-00009 | S547T/E548G/K549R/T550D |
| 545-00080 | G546N/S547A/E548A/K549R/T550D |
| 545-00700 | Q545T/S547A/E548T/K549/T550N |
| 545-16000 | Q545E/G546S/S547A/E548G/K549A |
| 549-00009 | K549R/T550D/I554A |
| 549-00080 | K549R/T550D/V552A/I554Y |
| 549-00700 | K549/T550N/N551K/V552T/D553T/I544L |
| 549-16000 | K549A/T550S/V552T/D553A/I554L |
| 551-00009 | I554A/E555D |
| 551-00080 | V552A/I554Y/E555S/K556D |
| 551-00700 | N551K/V552T/D553T/I554L/K556N |
| 551-16000 | V552T/D553A/I554L/E555D/K556N |
| 555-00009 | E555D |
| 555-00080 | E555S/K556D/I559L |
| 555-00700 | K556N/M558L/I559M |
| 555-16000 | E555D/K556N |
| 557-00009 | D561N |
| 557-00080 | I559L/D561S |
| 557-00700 | M558L/I559M/D561N |
| 561-00080 | D561S/R566K |
| 561-16000 | R566K |
| 563-00700 | T567P |
| 563-16000 | R566K/T567A |
| 489-00080 | K490T/S492T/A493G/D494Q |
| 489-00700 | S492L/A493D/D494Q |
| 495-00009 | Y500F |
| 499-00080 | E499N/Y500F/S501A/G504A |
| 501-00700 | S501A |
| 501-16000 | S501T/T506S |
| 503-00009 | T503P/T506S/K507S/Y508W |
| 505-00009 | T506S/K507S/Y508W/H509A |
| 507-00009 | K507S/Y508W/H509A |
| 509-00009 | H509A/D514N |
| 515-16000 | L516I/V517I |
| 531-00009 | E531D/K532R/Q536L |
| 531-00700 | E531D/K532R/Q536S |
| 531-16000 | E531D/Q536M |
| 533-00080 | Q536S/S537N |
| 561-00009 | D561N/R566K |
| 623-00789 | H627N |
| 635-00009 | L639M |
| 651-00089 | N656D |
| 653-16700 | S658P |
| 711-00080 | T713A/D715N |
| 713-00089 | T713A/D715N/N717E |
| 717-16000 | V719L/S721T |
| 489-00009 | K490T/S492V/A493T/D494Q |
| 489-16000 | S492K/A493T |
| 515-00009 | V517M |
| 537-00080 | S537N/V539I |
| 355-00009 | Q359E |
| 367-16789 | V372I |
| 377-00009 | N382D |
| 381-00700 | A386S |
| 405-00089 | T410Q |
| 405-00700 | T410E |
| 407-00080 | T410Q/S412T |
| 409-00009 | T410Q/T414E |
| 409-00700 | T410E/T414S |
| 411-00009 | T414E |
| 411-00080 | S412T |
| 411-00700 | T414S |
| 413-00009 | T414E/D417N |
| 413-10000 | D417E |
| 415-00009 | D417N |
| 513-00009 | D514N/V517M |
| 513-00080 | D514N/V517A |
| 519-00080 | P521I |
| 519-16000 | P521T |
| 521-00080 | P521I/S525T |

TABLE 1-continued

Hexapeptide scanning AAV2R585E-derived mutants

| Name of mutant[1] | Amino acid substitutions in addition to R585E |
|---|---|
| 521-00700 | P521V/S525T |
| 535-00009 | Q536L/V539S |
| 535-00080 | Q536S/S537N/V539I |
| 537-00009 | V539S |
| 539-00080 | V539I |
| 541-00080 | G546N |
| 541-00700 | Q545T |
| 541-16000 | Q545E/G546S |
| 547-00080 | S547A/E548A/K549R/T550D/V552A |
| 547-00700 | S547A/E548T/K549/T550N/N551K/V552T |
| 547-16000 | S547A/E548G/K549A/T550S/V552T |
| 553-00080 | I554Y/E555S/K556D |
| 553-00700 | D553T/I554L/K556N/M558L |
| 559-00700 | I559M/D561N |
| 567-16000 | T567A |
| 603-00780 | D608N |
| 637-10000 | H641N |
| 653-00089 | N656D/S658P |
| 655-00009 | N656D/S658P/T660A |
| 655-16000 | S658P/T659A/T660E |
| 657-00080 | S658P/T660A/S662N |
| 657-00700 | S658P/T659E/T660V/S662T |
| 659-00009 | T660A/S662N/A663K/A664D |
| 659-00080 | S662N/A663Q/A664S |
| 659-00700 | T659E/T660V/S662T/A663P |
| 659-16000 | T659A/T660E/A664T |
| 661-00080 | S662N/A663Q/A664S/F666L |
| 661-00700 | S662T/A663P |
| 661-16000 | A664T |
| 663-00009 | A663K/A664D/F666L/A667N |
| 663-00080 | A663Q/A664S/F666L/A667N |
| 663-00700 | A663P |
| 665-00089 | F666L/A667N |
| 667-00089 | A667N |
| 693-16000 | I698V |
| 699-00700 | Y704F |
| 701-00089 | N705Y |
| 701-00700 | Y704F/N705E |
| 701-16000 | N705A |
| 703-00009 | N705Y/V708N |
| 703-00080 | N705Y/V708T |
| 703-00700 | Y704F/N705E/S707Q/V708T |
| 703-16000 | N705A/V708A |
| 705-00080 | N705Y/V708T/N709S |
| 705-00700 | N705E/S707Q/V708T/N709G |
| 707-00009 | V708N/D711E |
| 707-00700 | S707QA/708T/N709G |
| 709-00009 | D711E/T713A |
| 709-00700 | N709G/T713A |
| 711-00009 | D711E/T713A/D715N |
| 711-00700 | T713A/T716S |
| 711-16000 | T716N |
| 713-00700 | T713A/T716S/N717Q |
| 715-00089 | D715N/N717E |
| 715-00700 | T716S/N717Q |
| 715-16000 | T716NA/V719L |
| 717-00089 | N717E |
| 717-00700 | N717Q |
| 729-16000 | N734P |
| 009-16789 | T14N |
| 019-16700 | Q21E/K24D |
| 025-16789 | P29A |
| 035-00009 | A35N/E36Q/R37Q/K39Q |
| 037-00700 | R37Q/H38K/K39Q/D41N/S42G |
| 063-16789 | E67A |
| 101-16780 | K105Q |
| 131-00009 | P135A/V136A |
| 137-00700 | G141A |
| 161-00780 | A162K |
| 161-16000 | A162T |
| 185-16780 | Q190E |
| 193-00089 | L198V |
| 195-00089 | L198V/T200S |
| 197-00009 | L198V/T200S/N201L |
| 197-00700 | G197S/L198V/T200S/N201G |
| 149-00780 | V151Q/E152R/153S |
| 149-16009 | V151Q |
| 155-00009 | S157A/T159I |
| 155-00780 | S157T/T159I |
| 017-16789 | Q21E |
| 019-00089 | Q21E/K24A |
| 023-00089 | K24A |
| 027-00009 | P29A/P31Q |
| 027-16780 | P29A/P31K |
| 029-00089 | P29A/P31Q/P34A |
| 031-00009 | P31Q/P34A/A35N/E36Q |
| 031-16780 | P31K/P34A/A35N/E36Q |
| 033-00009 | P34A/A35N/E36Q/R37Q |
| 033-16780 | P34A/A35N/E36Q/R37Q/H38K |
| 035-16780 | A35N/E36Q/R37Q/H38K/K39Q |
| 037-16080 | R37Q/H38K/K39Q/D41N/S42G |
| 039-00700 | K39Q/D41N/S42G |
| 039-16080 | K39Q/S42G |
| 041-00700 | D41N/S42G |
| 041-16080 | S42G |
| 051-00009 | F56G |
| 077-16789 | R81Q |
| 081-16709 | R81Q/D84K/S85A |
| 085-16789 | S85A |
| 087-16780 | K92R |
| 121-00009 | V125L |
| 125-06000 | L129F |
| 131-16780 | P135GA/136A |
| 143-00780 | H148P |
| 143-16009 | H148Q |
| 147-16009 | H148Q/V151Q |
| 159-00009 | T159I/A162S/Q164A |
| 161-00009 | A162S/Q164A |
| 163-00009 | Q164A/R168K |
| 163-16000 | R168K |
| 175-16780 | A179S/D180E |
| 183-00009 | L188I |
| 185-00009 | L188I/Q190E |
| 193-00700 | G197S/L198V |
| 195-00080 | L198V/T200P |
| 195-16000 | S196A/G197A/L198V/T200P |
| 197-16000 | G197A/L198V/T200P/N201T |
| 199-00009 | T200S/N201L |
| 199-00700 | T200S/N201G/M203V |
| 201-00080 | T205A |
| 201-00700 | N201G/M203V/T205A |
| 201-16000 | N201T/T205S |
| 203-16009 | T205S/S207G |
| 207-00009 | S207G/M211V |
| 209-00009 | M211V |
| 219-00009 | N223S |
| 229-00009 | T233Q |
| 231-00009 | T233Q/M235L |
| 231-16780 | M235L |
| 257-00009 | 262N |
| 257-00080 | S262N |
| 257-00700 | 262E |
| 259-00700 | S262E/Q263T/S264A |
| 261-16000 | Q263A/265T |
| 265-00009 | A266S |
| 267-00009 | H271A |
| 267-00780 | S267T/H271T |
| 269-00780 | H271T |
| 305-00009 | R310K |
| 307-00080 | N312S |
| 307-00700 | R310K/N312R |
| 311-00700 | N312R |
| 323-00009 | Q325D/D327N |
| 323-00080 | D327E |
| 325-00009 | Q325D/D327N/T329V/T330K |
| 325-00080 | D327E/T330K |
| 325-16700 | Q325T/T329V |
| 327-00009 | D327N/T329V/T330K |
| 329-00009 | T329V/T330K |
| 329-00080 | T330K |
| 339-16000 | T344S |
| 343-00009 | E347D |

TABLE 1-continued

Hexapeptide scanning AAV2R585E-derived mutants

| Name of mutant[1] | Amino acid substitutions in addition to R585E |
|---|---|
| 511-16000 | D514E/L516I |
| 553-16000 | D553A/I554L/E555D/K556N |
| 655-00700 | S658P/T659E/T660V |
| 657-00080 | S658P/S662N |
| 661-00009 | S662N/A663K/A664D/F666L |
| 707-00080 | V708T/N709S |
| 707-16000 | V708A |
| 709-00080 | N709S/T713A |
| 517-00080 | V517A/P521I |
| 517-00700 | P521V |
| 517-16000 | V517I/P521T |
| 721-16000 | S721T |
| 155-16000 | T159I |
| 157-00009 | S157A/T159I/A162S |
| 157-16000 | T159I/A162T |
| 023-16700 | K24D |
| 029-16780 | P29A/P31K/P34A |
| 037-00009 | R37Q/K39Q/D41N/S42A |
| 039-00009 | K39Q/D41N/S42A |
| 041-00009 | D41N/S42A |
| 079-00080 | R81Q/D84Q |
| 079-16709 | R81Q/D84K |
| 081-00080 | R81Q/D84Q/S85A |
| 083-16709 | D84K/S85A |
| 147-00780 | H148P/V151Q/E152R/153S |
| 175-00009 | A179T/D180E |
| 189-16000 | Q190E/A194T |
| 191-16000 | A194T/S196A |
| 193-16000 | A194T/S196A/G197A/L198V |
| 195-00700 | G197S/L198V/T200S |
| 199-00080 | T200P |
| 199-16000 | T200P/N201T |
| 201-00009 | N201L/T205S |
| 203-00080 | T205A/S207G |
| 207-16780 | S207G |
| 219-16700 | S224A |
| 259-00009 | 262N/Q263T |
| 259-16000 | Q263A |
| 261-00009 | 262N/Q263T/A266S |
| 321-00009 | Q325D |
| 335-00780 | V340I |
| 339-00700 | V340I/T344S |
| 083-00080 | D84Q/S85A |
| 159-00780 | T159I/A162K |
| 203-00700 | M203V/T205A/S207G |
| 259-00080 | S262N/263G/Q264T |
| 261-00080 | S262E/Q263T/S264A/A266S |
| 263-00009 | Q263T/265G/A266S |
| 263-00080 | Q263T/267G/S270T |
| 263-00700 | Q263T/S264A/A266S/S267T |
| 265-00700 | A266S/S267T |
| 321-16700 | Q325T |
| 261-00080 | S262N/263G/Q264T/267G |
| 265-00080 | S267T |
| 327-16700 | T329V |
| 487-00009 | K490T/S492V |
| 487-00700 | S492L |
| 497-00780 | E499N/Y500F/S501A |
| 153-00009 | S157A |
| 153-00780 | S157T |
| 157-00780 | S157T/T159I/A162K |

[1]The following system is used to name the hexapeptide scanning AAV2R585E mutants. The left three digits indicate the first amino acid position of the hexapeptide based on AAV2 VP1. The right five digits indicate AAV serotype from which each hexapeptide is derived: 10000, AAV1; 06000, AAV6; 00700, AAV7; 00080, AAV8; and 00009, AAV9. When a hexapeptide amino acid sequence is shared with multiple serotypes, the right five digits have more than one positive integer.
[2]Alternative names used in Adachi K et al., Nat Commun 5, 3075 (2014).
[3]Alternative names used in Asokan et al., Nature Biotechnology 28, 79-83 (2010).

EXAMPLES

The following examples are illustrative of disclosed methods. In light of this disclosure, those of skill in the art will recognize that variations of these examples and other examples of the disclosed method would be possible without undue experimentation.

Example 1—Development of an In Vitro IP-Based AAV Barcode-Seq Method to Identify Anti-AAV Antibody Epitopes IP conditions were optimized using a recombinant AAV9 vector, anti-AAV9 mouse sera, and protein A/G agarose beads. Then, a DNA-barcoded AAV HP scanning capsid mutant library comprising 78 AAV clones was produced, which included nineteen AAV2R585E-derived HP mutants and five AAV9-derived HP mutants that spanned a 14-amino-acid region in and flanking the vicinity of the highest peak of the AAV1, AAV2, AAV7, AAV8, and AAV9 capsids. Using this library and anti-AAV1, anti-AAV2, anti-AAV7, anti-AAV8, anti-AAV9, and naive mouse sera collected from four mice per serotype/native, IP was performed and AAV library genomes were recovered from both immunoprecipitates and supernatants, which were then subjected to the AAV Barcode-Seq analysis. As a result, it was found that mutants harboring AAV1-, AAV2-, AAV7-, AAV8-, and AAV9-derived peptides spanning eight amino acids within the vicinity of the highest peak, but not other mutants or the control AAV2R585E or AAV9, were clearly captured by the corresponding anti-AAV serotype sera of some, if not all, of the immunized mice, indicating that the identified peptides constitute a dominant epitope. Thus, these results demonstrated that a combination of AAV Barcode-Seq with IP can be a substantially easy and effective approach to map anti-AAV antibody epitopes in a high-throughput manner.

Example 2—Generation of an HP Scanning AAV Mutant Library Covering the Entire AAV2 Region Similar to Example 1, 153 HP scanning AAV9 mutants that cover the entire region of AAV2 can be created.

Example 3—Generation of a dsAAV9-HP-U6-VBCLib-2 Library Containing a Total of 338 AAV Clones To map anti-AAV2 antibody epitopes, a total of 153 AAV helper plasmids expressing the AAV2 Rep protein and various AAV9 capsid mutant proteins each of which contained a different hexapeptide region derived from the AAV2 capsid (AAV9-HP scanning mutants) were constructed. Using these AAV helper plasmids, a DNA/RNA-barcoded dsAAV-U6-VBCLib library packaged with the AAV9-HP scanning mutants was produced. This library, termed dsAAV9-HP-U6-VBCLib-2, contained all the AAV9-HP mutants listed in Table 2 (2 clones per mutant). It also contained AAV2 (2 clones) and the two reference controls, AAV2R585E and AAV9 (15 clones each). The titer of this library was $2.8 \times 10^{13}$ vector genomes (vg)/ml.

TABLE 2

Hexapeptide scanning AAV9-derived mutants

| Name of mutant[4] | Amino acid substitutions |
|---|---|
| 009-00002 | N14T |
| 017-00002 | E21Q |
| 019-00002 | E21Q/A24K |
| 023-00002 | A24K |
| 025-00002 | A29P |

TABLE 2-continued

Hexapeptide scanning AAV9-derived mutants

| Name of mutant[4] | Amino acid substitutions |
|---|---|
| 027-00002 | A29P/Q31P |
| 029-00002 | A29P/Q31P/A34P |
| 031-00002 | Q31P/A34P/N35A/Q36E |
| 033-00002 | A34P/N35A/Q36E/Q37R |
| 035-00002 | N35A/Q36E/Q37R/Q39K |
| 037-00002 | Q37R/Q39K/N41D/A42S |
| 039-00002 | Q39K/N41D/A42S |
| 041-00002 | N41D/A42S |
| 051-00002 | G56F |
| 063-00002 | A67E |
| 077-00002 | Q81R |
| 079-00002 | Q81R/K84D |
| 081-00002 | Q81R/K84D/A85S |
| 083-00002 | K84D/A85S |
| 085-00002 | A85S |
| 121-00002 | L125V |
| 131-00002 | A135P/A136V |
| 143-00002 | Q148H |
| 147-00002 | Q148H/Q151V |
| 149-00002 | Q151V |
| 153-00002 | A157S |
| 155-00002 | A157S/I159T |
| 157-00002 | A157S/I159T/S162A |
| 159-00002 | I159T/S162A/A164Q |
| 161-00002 | S162A/A164Q |
| 163-00002 | A164Q/K168R |
| 165-00002 | K168R |
| 175-00002 | T179A/E180D |
| 183-00002 | I188L |
| 185-00002 | I188L/E190Q |
| 189-00002 | E190Q |
| 193-00002 | V198L |
| 195-00002 | V198L/S200T |
| 197-00002 | V198L/S200T/L201N |
| 199-00002 | S200T/L201N |
| 201-00002 | L201N/S205T |
| 203-00002 | S205T/G207S |
| 207-00002 | G207SA/211M |
| 209-00002 | V211M |
| 219-00002 | S223N |
| 229-00002 | Q233T |
| 231-00002 | Q233T/L235M |
| 235-00002 | L235M |
| 257-00002 | N262S/S263 |
| 259-00002 | N262S/S263/T264Q |
| 261-00002 | N262S/S263/T264Q/G267/G268A |
| 264-00002 | T264Q/G267/S268A |
| 267-00002 | S268A |
| 269-00002 | A273H |
| 323-00002 | D327Q |
| 325-00002 | D327Q/N329D |
| 327-00002 | D327Q/N329D/V331T/K332T |
| 329-00002 | N329D/V331T/K332T |
| 331-00002 | V331T/K332T |
| 345-00002 | D349E |
| 357-00002 | E361Q |
| 369-00002 | I374V |
| 379-00002 | D384N |
| 407-00002 | Q412T |
| 411-00002 | Q412T/E416T |
| 413-00002 | E416T |
| 415-00002 | E416T/N419D |
| 417-00002 | N419D |
| 445-00002 | K449R |
| 447-00002 | K449R/I451N/N452T |
| 449-00002 | K449R/I451N/N452T/G453PS |
| 451-00002 | I451N/N452T/G453PS/S454G/G455T |
| 453-00002 | G453PS/S454G/G455T/Q456T/N457T |
| 454-00002 | S454G/G455T/Q456T/N457T/Q459S |
| 456-00002 | Q456T/N457T/Q459S/T460R |
| 458-00002 | Q459S/T460R/K462Q |
| 460-00002 | T460R/K462Q/V465Q |
| 462-00002 | K462Q/V465Q |
| 464-00002 | V465Q/P468A |
| 466-00002 | P468A/N470D/M471I |
| 468-00002 | P468A/N470D/M471I/A472R/V473D |
| 470-00002 | N470D/M471I/A472R/V473D/G475S |
| 472-00002 | A472R/V473D/G475S |
| 474-00002 | G475S/Y478W/I479L |
| 476-00002 | Y478W/I479L |
| 478-00002 | Y478W/I479L/S483C |
| 480-00002 | S483C |
| 486-00002 | T491K |
| 488-00002 | T491K/V493S |
| 490-00002 | T491K/V493S/T494A/Q495D |
| 492-00002 | V493S/T494A/Q495D |
| 494-00002 | T494A/Q495D |
| 496-00002 | F501Y |
| 498-00002 | F501Y/A502S |
| 500-00002 | F501Y/A502S/P504T |
| 502-00002 | A502S/P504T/S507T |
| 504-00002 | P504T/S507T/S508K/W509Y |
| 506-00002 | S507T/S508K/W509Y/A510H |
| 508-00002 | S508K/W509Y/A510H |
| 510-00002 | A510H/N515D |
| 512-00002 | N515D |
| 514-00002 | N515D/M518V |
| 516-00002 | M518V |
| 524-00002 | E529D |
| 526-00002 | E529D/G530D |
| 528-00002 | E529D/G530D/D532E/R533K |
| 530-00002 | G530D/D532E/R533K |
| 532-00002 | D532E/R533K/L537Q |
| 534-00002 | L537Q |
| 536-00002 | L537Q/S540V |
| 538-00002 | S540V |
| 544-00002 | T548S/G549E |
| 546-00002 | T548S/G549E/R550K/D551T |
| 550-00002 | R550K/D551T/A555I |
| 552-00002 | A555I/D556E |
| 556-00002 | D556E |
| 558-00002 | N562D |
| 562-00002 | N562D/K567R |
| 564-00002 | K567R |
| 572-00002 | S576Q |
| 574-00002 | S576Q/Q579S |
| 576-00002 | S576Q/Q579S/A581S |
| 578-00002 | Q579S/A581S |
| 580-00002 | A581S/H584L |
| 582-00002 | H584L/S586R/A587G |
| 584-00002 | H584L/S586R/A587G/Q588N/A589R |
| 586-00002 | S586R/A587G/Q588N/A589R |
| 588-00002 | Q588N/A589R/Q592A |
| 590-00002 | Q592A/G594A/W595D |
| 592-00002 | Q592A/G594A/W595D/Q597N |
| 594-00002 | G594A/W595D/Q597N/N598T |
| 596-00002 | Q597N/N598T/I601V |
| 598-00002 | N598T/I601V |
| 600-00002 | I601V |
| 624-00002 | N628H |
| 636-00002 | M640L |
| 652-00002 | D657N |
| 654-00002 | D657N/P659S |
| 656-00002 | D657N/P659S/A661T |
| 658-00002 | P659S/A661T/N663S |
| 660-00002 | A661T/N663S/K664A/D665A |
| 662-00002 | N663S/K664A/D665A/L667F |
| 664-00002 | K664A/D665A/L667F/N668A |
| 666-00002 | L667F/N668A |
| 668-00002 | N668A |
| 702-00002 | Y706N |
| 704-00002 | Y706N/N709V |
| 708-00002 | N709V/E712D |
| 710-00002 | E712D/A714T |
| 712-00002 | E712D/A714T/N716D |
| 714-00002 | A714T/N716D/E718N |
| 716-00002 | N716D/E718N |
| 718-00002 | E718N |

TABLE 2-continued

Hexapeptide scanning AAV9-derived mutants

Name of mutant[4]    Amino acid substitutions

[4]The following system is used to name the hexapeptide scanning AAV9 mutants. The left three digits indicate the first amino acid position of the hexapeptide based on AAV9 VP1. The right five digits indicate AAV serotype from which each hexapeptide is derived: 10000, AAV1; 06000, AAV6; 00700, AAV7; 00080, AAV8; and 00009, AAV9; and 00002, AAV2. When a hexapeptide amino acid sequence is shared with multiple serotypes, the right five digits have more than one positive integer.

Example 4—Optimization of the IP-Seq Procedure Using Protein A/G Magnetic Beads In preliminary IP-Seq experiments, a traditional protein A/G agarose beads-based method for immunoprecipitation of anti-AAV capsid antibody-binding AAV particles was used. In this set of experiments, the IP procedure was optimized using magnetic beads, which have become more favorable than agarose beads in various aspects such as easy handling and faster rate of binding. During the course of the optimization using AAV2 particles and Pierce Protein A/G Magnetic Beads (Thermo Scientific, Product No. 88804), it was found that a significant fraction of input AAV2 viral particles in the IP reaction tubes can bind nonspecifically to the magnetic beads. To prevent this nonspecific binding, a series of blocking reagents was tested including 1%, 2%, 4%, and 8% bovine serum albumin (BSA, Sigma, A3294-500G) in PBS (BioWhittaker, 17-516F) and ethanolamine (Sigma-Aldrich, E0135)/glycine (Sigma Life Science, G8898-1KG) solution. The ethanolamine/glycine solution was prepared with 50 mM Tris, 200 mM glycine, 1% Tween-20 (Sigma, P5927), 200 mM ethanolamine, pH 10.6. As a result, it was found that 2% BSA in PBS yielded the best blocking efficiency. Since buffer stringency could affect the IP procedure, low stringency buffer (PBS), medium stringency buffer (1% Triton X-100 (Sigma, T8532) in TBS, pH 7.4) and high stringency buffer (RIPA buffer) in the presence of 2% BSA was tested. It was found that low stringency IP buffer (PBS) had the lowest level of AAV particles nonspecifically bound to magnetic beads. Therefore, the subsequent experiments were done using 2% BSA in PBS as the IP buffer for IP-Seq. Various combinations of temperature and incubation time were compared at each step (at 37° C. for 1 hour vs. at 4° C. overnight), and no significant difference was found. Based on these observations in the optimization experiments, the IP-Seq procedure was established as follows:

(1) Wash 0.20 mg (20 µL) of Pierce Protein A/G Magnetic Beads (Thermo Scientific, Product No. 88804) with 1 mL PBS.

(2) Incubate with rotation the washed Pierce Protein A/G Magnetic Beads and an anti-AAV antibody-containing sample in 500 µL PBS at 37° C. for 1 hour. In the experiments described here, the antibody-containing samples were either mouse monoclonal A20 antibody (the antibody against intact AAV2 particles, 500 ng (10 µL) per IP reaction) or sera from the mice immunized with intravenous injection of $1 \times 10^{11}$ vg of AAV2-CMV-lacZ (20 µL per IP reaction). However, any samples containing anti-AAV antibody including anti-AAV antibody-positive human sera can be analyzed using the IP-Seq method described herein.

(3) Discard the PBS containing the sample.

(4) Block nonspecific binding by incubating the magnetic beads with 500 µL of PBS containing 2% BSA at 37° C. for 1 hour.

(5) Discard the blocking buffer.

(6) Incubate the BSA-treated magnetic beads with $1 \times 10^9$ vg of a DNA/RNA-barcoded dsAAV-U6-VBCLib library in 350 µL of PBS containing 2% BSA at 37° C. for 1 hour. The amount of input viral particles can be in a range from $5 \times 10^7$ vg to $1 \times 10^9$ vg.

(6) Save the supernatant for the AAV Barcode-Seq analysis.

(7) Wash the magnetic beads with 500 µL of PBS twice.

(8) Extract DNA from the supernatant and the magnetic beads with Proteinase K treatment (Proteinase K from Ambion) and Wako DNA Extractor Kit (Wako Chemicals, Richmond, USA).

(9) Resuspend the dried DNA pellets in 10-20 µL of TE.

(10) Amplify virus DNA barcodes using 1/10 of the above-described DNA preparation.

(11) Combine PCR products and subject them to Illumina sequencing.

Figure 9:
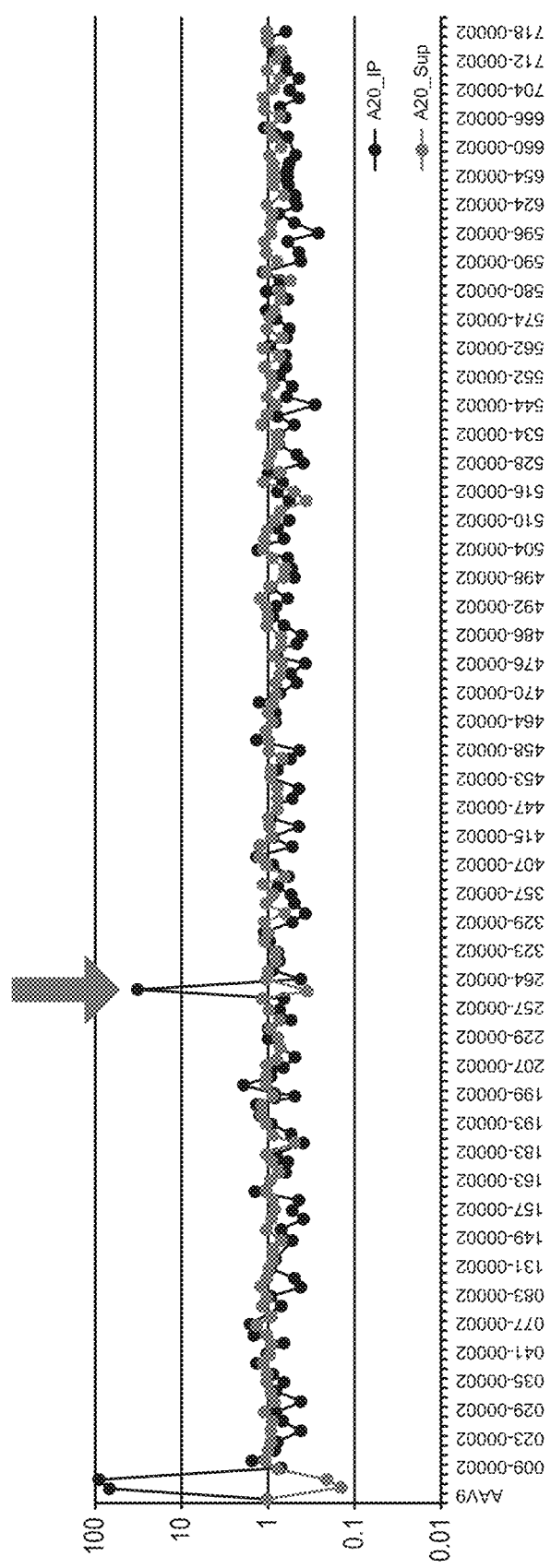
FIG. 9 is a graph depicting anti-AAV2 capsid mouse monoclonal antibody (A20) epitope identification by the magnetic beads-based IP-Seq analysis in conjunction with the dsAAV9-HP-U6-VBCLib-2 library. $1 \times 10^9$ vg of the dsAAV9-HP-U6-VBCLib-2 library was reacted with Pierce Protein A/G Magnetic Beads coated with the A20 antibody, and subjected to immunoprecipitation. Subsequently, viral genomic DNAs were extracted from magnetic beads-bound and unbound AAV particles in the IP precipitates (A20_IP) and the IP supernatants (A20_Sup), respectively, and a demographic change of the library composition in the IP precipitates (A20_IP) and the IP supernatants (A20_Sup) was determined by the AAV Barcode-Seq analysis. The relative quantity of each clone (2 clones per mutant) determined by Illumina barcode sequencing read numbers was normalized with the Illumina sequencing read numbers of the reference control AAV9. The Y-axis shows Phenotypic Difference (PD) values of each mutant relative to the control AAV9. The X-axis shows different AAV strains. They are AAV9, AAV2R585E, AAV2, 009-00002, . . . , 718-00002 from the left to the right. Due to space limitations, not all the AAV2 strains are labeled. Plotted are the averages of the relative quantities of two different clones carrying the same HP mutation. An arrow indicates the mutant 261-00002 harboring a heterologous AAV2-derived peptide that binds to the A20 antibody (261-SSQSGA-266 (SEQ ID NO:50)). Another peak to the leftmost represents AAV2R585E and AAV2.

Example 5—Epitope Mapping of a Mouse Monoclonal Antibody Against Intact AAV2 Capsid A20 may be the most widely used, commercially available mouse monoclonal antibody against intact AAV2 capsid. This antibody is available from American Research Product Inc. (Catalog No. 03-61055). In order to map A20 antibody epitopes on the AAV2 capsid, IP was performed using 500 ng of A20 antibody and $1 \times 10^9$ vg of dsAAV9-HP-U6-VBCLib-2. Viral DNA recovered from the IP supernatant and magnetic beads were subjected to the AAV Barcode-Seq analysis. In brief, Pierce Protein A/G Magnetic Beads were first coated with the A20 antibody at 37° C. for 1 hour, blocked with PBS/2% BSA at 37° C. for 1 hour, and then reacted with $1 \times 10^9$ vg of dsAAV9-HP-U6-VBCLib-2 at 37° C. for 1 hour. This library contained 338 AAV clones composed of 153 AAV9-HP mutants, AAV2 and two reference controls (AAV2R585E and wild-type AAV9, 15 clones each). These AAV9-HP mutants were created to identify anti-AAV2 antibody epitopes by scanning the entire AAV2 capsid region with a set of AAV2 capsid protein-derived hexapeptides. Two of the 153 AAV9-HP mutants, 584-00002 and 586-00002 (see Table 2), could not be produced at levels sufficient for the downstream analysis; therefore, they are not included in the dataset. As expected, AAV2 and AAV2R585E bound to A20 efficiently, resulting in substantial enrichment and reduction of AAV2 and AAV2R585E viral genomes in the IP fraction and the supernatant, respectively (see FIG. 9). There is a clear peak on 261-00002 showing more than 30-fold enrichment in the IP fraction (see FIG. 9). This mutant carries 261-SSQSGA-266 (SEQ ID NO:50) of AAV2 capsid in place of 261-SNSTSGGS-268 (SEQ ID NO:51) of AAV9 capsid; therefore, 261-SSQSGA-266 (SEQ ID NO:50) should include an A20 antibody epitope. This finding is in keeping with the previous cryo-electron microscopy study showing that S261, Q263, and S264 are among the amino acids found in the A20 binding footprint (McCraw DM et al., Virology 431 (1-2), 40-49 (2012)). No other epitopes were identified by this approach.

Example 6—Epitope Mapping of Mouse Polyclonal Antibodies Against AAV2 Capsid

Figure 10A:
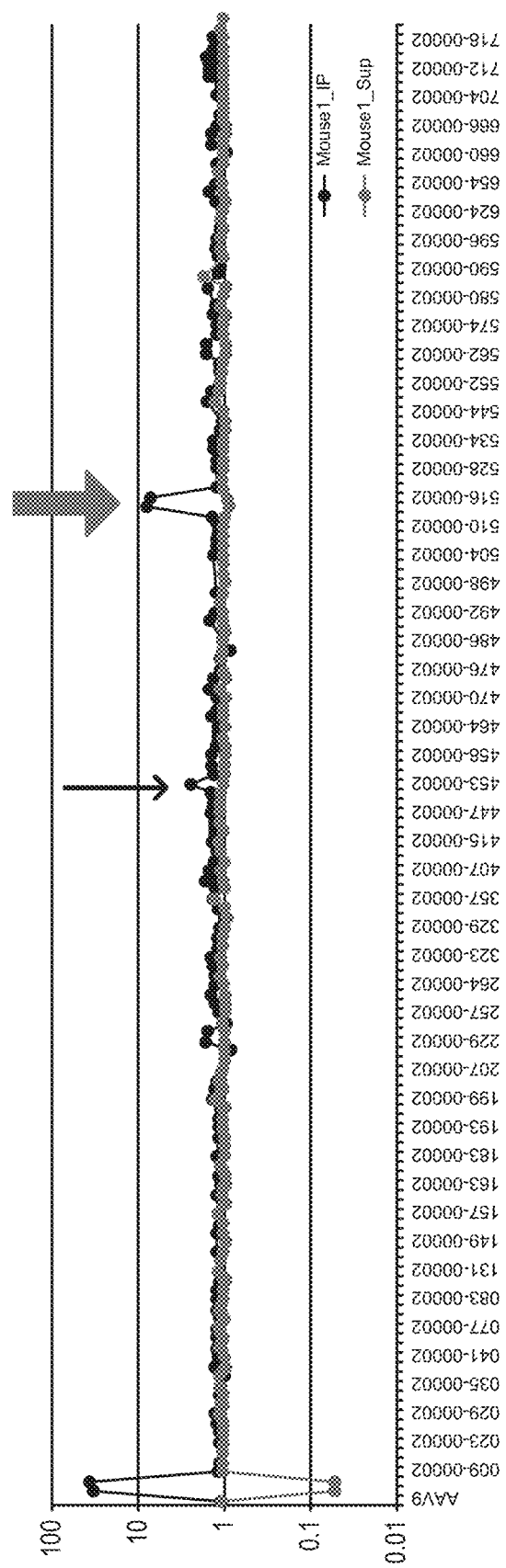
FIGS. 10A, 10B, 10C, and 10D are graphs depicting anti-AAV2 mouse polyclonal antibody epitope identification by the magnetic beads-based IP-Seq analysis in conjunction with the dsAAV9-HP-U6-VBCLib-2 library. Four 8-week-old C57BL/6 male mice (Mouse 1, 2, 3 and 4 in FIGS. 10A, 10B, 10C, and 10D, respectively) were injected intravenously with AAV2-CMV-lacZ vector at a dose of $1 \times 10^{11}$ vg/mouse. Serum samples containing anti-AAV2 neutralizing antibodies were collected 3 weeks post-injection and subjected to the IP-Seq analysis for epitope mapping. Demographic change of the library composition in the IP precipitates (Mouse1, 2, 3 and 4_IP) and the IP supernatants (Mouse1, 2, 3, and 4_Sup) were determined by the AAV Barcode-Seq analysis. The relative quantity of each clone (2 clones per mutant) determined by Illumina barcode sequencing read numbers was normalized with the Illumina sequencing read numbers of the reference control AAV9. The Y-axis shows Phenotypic Difference (PD) values of each mutant relative to the control AAV9. The X-axis shows different AAV strains. They are AAV9, AAV2R585E, AAV2, 009-00002, . . ., 718-00002 from the left to the right. Due to space limitations, not all the AAV2 strains are labeled. Plotted are the averages of the relative quantities of two different clones carrying the same HP mutation. Gray arrows, in FIGS. 10A-10D, indicate the two hexapeptide mutants containing the dominant epitope, 513-RDSLVNPG-520 (SEQ ID NO:52). The thick black arrow, in FIG. 10D, indicates the same epitope identified for the A20 antibody. Thin black arrows, in FIGS. 10A-10C, also indicate mutants that may contain epitopes. The peak to the leftmost represents AAV2R585E and AAV2.
Figure 10B:
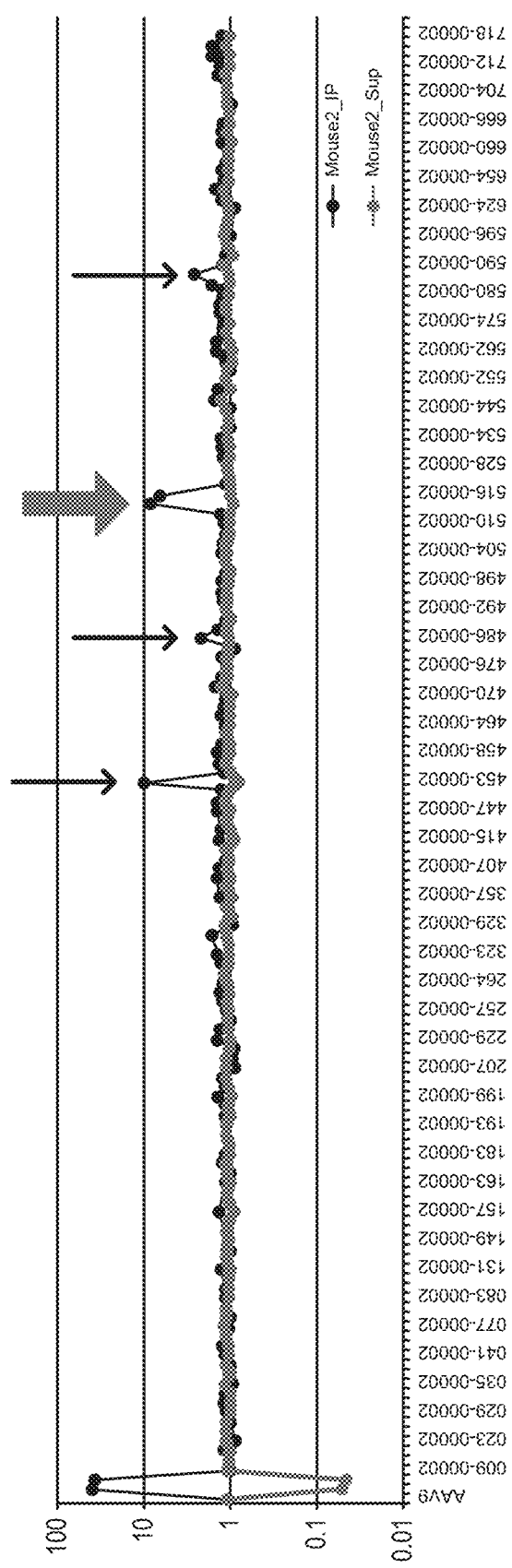
Figure 10C:
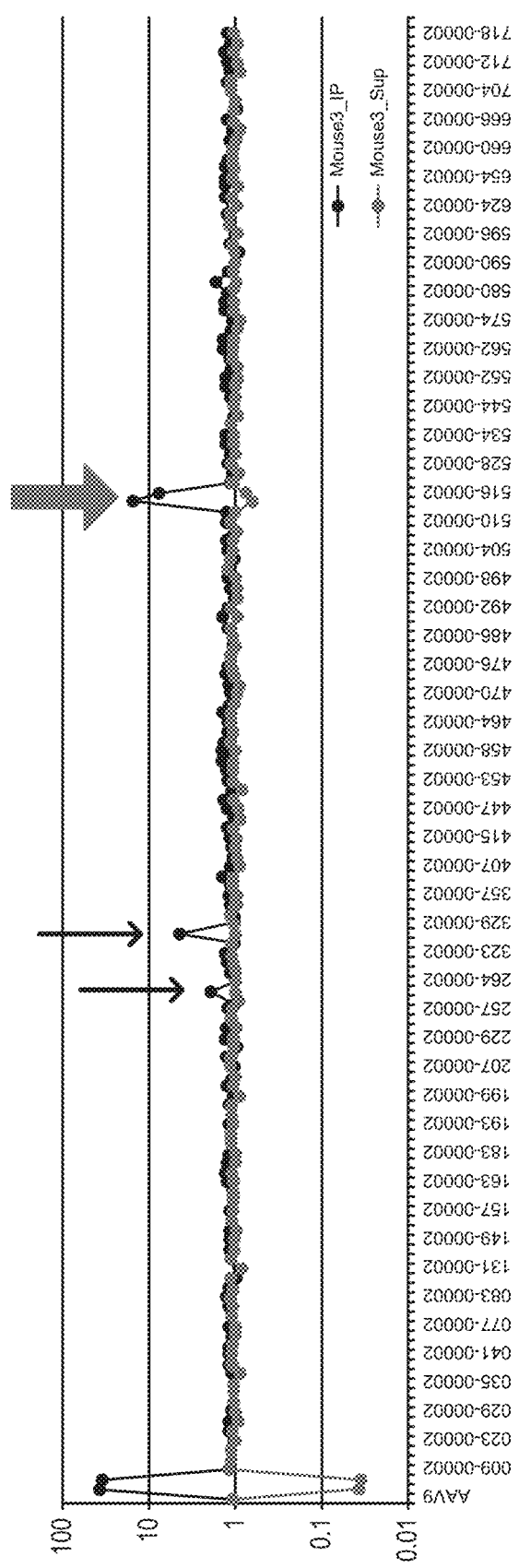
Figure 10D:
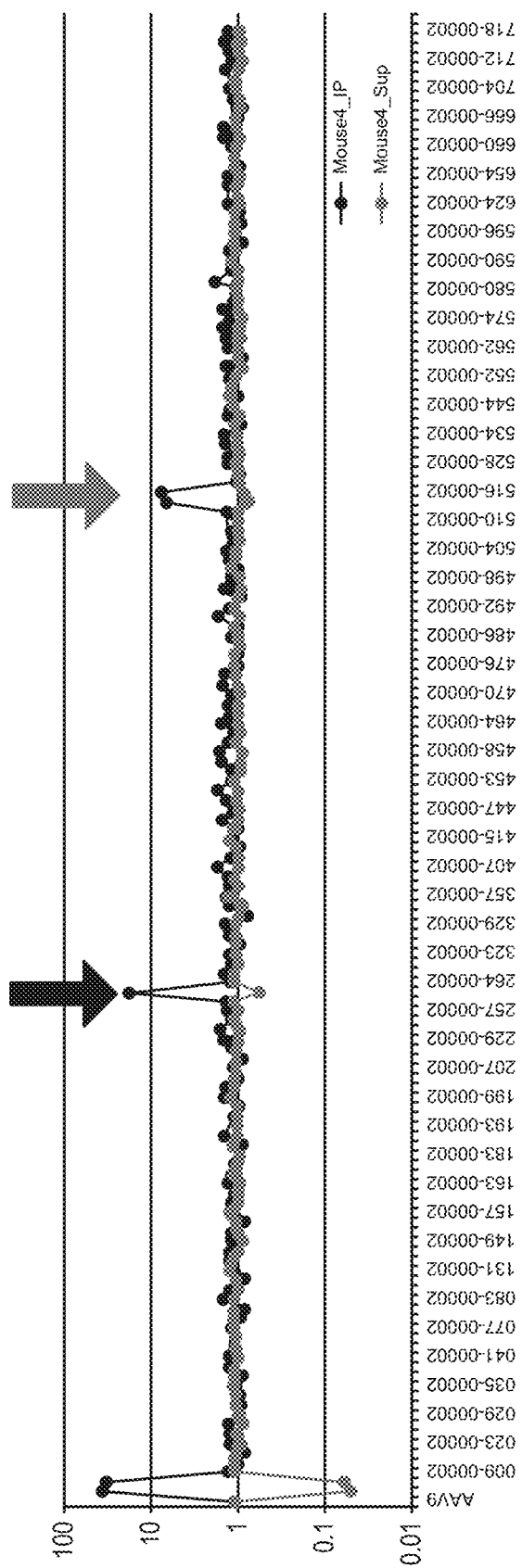

The same magnet beads-based IP-Seq analysis for epitope mapping was applied to anti-AAV2 antibody-positive sera collected from 4 C57BL/6 male mice. The serum samples used for this analysis were the same as those used for the data presented in FIG. 6, for which a traditional agarose beads-based immunoprecipitation was used. Briefly, 8-week-old C57BL/6 male mice (Mouse 1, 2, 3 and 4) were injected intravenously with AAV2-CMV-lacZ vector at a dose of 1×10$^{11}$ vg/mouse. Serum samples containing anti-AAV2 neutralizing antibodies were collected 3 weeks post-injection. 20 µL of each serum sample was then subjected to the magnetic beads-based IP-Seg analysis for epitope mapping using the dsAAV9-HP-U6-VBCLib-2 library, as described above. In the preliminary agarose beads-based IP-Seg analysis using the dsAAV-HP-U6-VBCLib-1 that contained only 5 AAV9-HP mutants, 451-PSGTTT-456 (SEQ ID NO:3) was identified as an epitope of polyclonal anti-AAV2 antibodies developed in Mouse 2 (see FIG. 6). This was reproduced in this new IP-Seg procedure (see FIG. 10B). In addition, the absence of this epitope in Mouse 3 and 4 (see FIGS. 10C and 10D), and a weak reactivity to this epitope in Mouse 1 (see FIG. 10A) was also reproduced. By scanning the entire AAV2 capsid region with hexapeptides, a dominant epitope that was found in all the mice could be identified, 513-RDSLVNPG-520 (SEQ ID NO:52) of the AAV2 capsid, based on the observation that there is a peak at 514-00002 (513-RDSLVN-518 (SEQ ID NO:53)) and 516-00002 (515-SLVNPG-520 (SEQ ID NO:54)) (see FIGS. 10A-D). Other epitopes, 325-QNDGTT-330 (SEQ ID NO:55) (based on a peak at 327-00002 in Mouse 3, see FIG. 10C) and 261-SSQSGA-266 (SEQ ID NO:50) (based on a peak at 261-00002 in Mouse 4, see FIG. 10D) could also be identified. The latter epitope is the same as that for the A20 mouse monoclonal antibody and a modest peak at this position was also found in Mouse 3 (see FIG. 10C). Moreover, modest peaks were also found at 486-00002 and 588-00002 in Mouse 2 (see FIG. 10B), indicating that 485-QQRVSK-490 (SEQ ID NO:56) and 587-NRQAAT-592 (SEQ ID NO:57) are epitopes.

Example 7—Development of Anti-AAV Neutralizing Antibody-Escaping AAV Capsid Mutants The IP-Seg analysis of anti-AAV antibody-positive mouse sera has revealed that 513-RDSLVNPG-520 (SEQ ID NO:52) may be the most dominant epitope for anti-AAV2 antibodies. The RDSLVNPG (SEQ ID NO:52) is an evolutionarily conserved region across different AAV serotypes and variants, and therefore this region may likely be the dominant epitope for anti-AAV antibodies. In addition, this study indicated that the same topological region around 453-456 is found to be a common epitope across different AAV strains; i.e., 452-QSGSAQNK-459 (SEQ ID NO:5) in the AAV1 capsid, 451-PSGTTT-456 (SEQ ID NO:3) in the AAV2 capsid, 453-NPGGTAG-459 (SEQ ID NO:6) in the AAV7 capsid and 453-GCGQN-457 (SEQ ID NO:58) in the AAV9 capsid. Thus, introduction of amino acid mutations in the RDSLVNPG (SEQ ID NO:52)-corresponding regions and/or in the vicinity of the 453-456 region, or swapping the amino acids in these regions, may offer an effective approach to develop anti-AAV neutralizing antibody-escaping AAV mutants. In addition, other epitope motifs that have been identified so far and that may be identified using the method described herein may be the targets for capsid mutagenesis aimed at creating novel anti-AAV neutralizing antibody-escaping AAV capsid mutants.

It will be apparent to those having skill in the art that many changes may be made to the details of the above-described embodiments without departing from the underlying principles of the invention. The scope of the present invention should, therefore, be determined only by the following claims.

The invention claimed is:

1. An AAV9 viral vector comprising, an antibody neutralizing mutation in amino acids 453-457 in an AAV9 capsid.

2. The vector of claim 1, wherein the antibody neutralizing mutation is a mutation to an alanine.

* * * * *